US006153201A

United States Patent [19]
Rose et al.

[11] Patent Number: 6,153,201
[45] Date of Patent: Nov. 28, 2000

[54] ORAL IMMUNIZATION WITH PAPILLOMAVIRUS VIRUS-LIKE PARTICLES

[75] Inventors: Robert C. Rose, Dansville, N.Y.; Anna-Lise Williamson; Edward P. Rybicki, both of Cape Town, South Africa

[73] Assignees: University of Rochester, Rochester, N.Y.; University of Cape Town, South Africa

[21] Appl. No.: 09/087,312

[22] Filed: May 29, 1998

Related U.S. Application Data

[63] Continuation-in-part of application No. 08/207,309, Mar. 7, 1994, which is a continuation-in-part of application No. 08/028,517, Mar. 9, 1993.

[51] Int. Cl.[7] .............................. A61K 39/12; C12N 7/00
[52] U.S. Cl. ..................................... 424/204.1; 435/235.1
[58] Field of Search ...................... 424/204.1; 435/235.1

[56] References Cited

U.S. PATENT DOCUMENTS

| | | |
|---|---|---|
| 4,777,349 | 10/1988 | Schoolnik et al. . |
| 4,870,023 | 9/1989 | Fraser et al. . |
| 5,041,385 | 8/1991 | Kingsman et al. . |
| 5,045,447 | 9/1991 | Minson . |
| 5,057,411 | 10/1991 | Lancaster et al. . |
| 5,071,757 | 12/1991 | Kreider et al. . |
| 5,169,766 | 12/1992 | Schuster et al. . |
| 5,346,811 | 9/1994 | Galindo-Castro et al. . |
| 5,437,951 | 8/1995 | Lowy et al. . |

FOREIGN PATENT DOCUMENTS

| | | |
|---|---|---|
| WO 92/00364 | 1/1992 | Australia . |
| 0 343 783 A2 | 4/1989 | European Pat. Off. . |
| 0 390 252 A2 | 3/1990 | European Pat. Off. . |
| WO 92/10513 | 6/1992 | WIPO . |
| WO 94/00152 | 6/1992 | WIPO . |
| WO 92/16636 | 10/1992 | WIPO . |
| WO 93/02184 | 2/1993 | WIPO . |
| WO 94/05792 | 3/1994 | WIPO . |
| 97/02835 | 1/1997 | WIPO .............................. A61K 39/00 |

OTHER PUBLICATIONS

Reichman et al., "Papillomaviruses," in Mandell et al., eds. *Principles and Practice of Infectious Diseases*, 3rd Ed., New York, New York:Churchill Livingstone, pp. 1191–1200 (1990).

Crum et al., "Human Papillomavirus Infection and Cervical Neoplasia: New Perspectives," *Int. J. Gynecol. Pathol.*, 3:376–388 (1984).

Zur–Hausen, "Genital Papillomavirus Infections," in Rigby, eds., *Virues and Cancer*, Cambridge, UK:Cambridge University Press, pp. 83–90 (1985).

Koutsky et al., "Epidemiology of Genital Human Papillomavirus Infection," *Epidemiol. Rev.*, 10:122–163 (1988).

Bonnez et al., "The PstI–XhoII Restriction Fragment of the HPV–6b L1 ORF Lacks Immunological Specificity as Determined by SERA from HPV 6 Condyloma Acuminatum Patients and Controls," in Howley, eds., *Papillomaviruses: UCLA Symp. Mol.Cell Biol.,New Series*, vol. 124, New York, New York:Wiley–Liss, Inc., pp. 77–80 (1990).

Jenison et al., "Identification of Immunoreactive Antigens of Human Papillomavirus Type 6B by Using *Escherichia coli*—Expressed Fusion Proteins," *J. Virol.*, 62:2115–2123 (1988).

Li et al., "Identification of the Human Papillomavirus Type 6b L1 Open Reading Frame Protein in Condylomas and Corresponding Antibodies in Human Sera," *J. Virol.*, 61:2684–2690 (1987).

Steele et al., "Humural Assays of Human Sera to Disrupted and Nondisrupted Epitopes of Human Papillomavirus Type 1," *Virology*, 174:388–398 (1990).

Strike et al., "Expression in *Escherichia coli* of Seven DNA Segments Comprising the Complete L1 and L2 Open Reading Frames of Human Papillomavirus Type 6b and the Localization of the 'Common Antigen Region,'" *J. Gen. Virol.*, 70:543–555 (1989).

Kienzler et al., "Humoral and Cell–Mediated Immunity to Human Papillomavirus Type 1 (HPV–1) in Human Warts," *Br. J. Dermatol.*, 108:665–672 (1983).

Pfister et al., "Seroepidemiological Studies of Human Papilloma virus (HPV–1) Infections," *Int. J. Cancer*, 21:161–165 (1978).

Kreider et al., "Laboratory Production In vivo of Infectious Human Papillomavirus Type 11," *J. Virol.*, 61:590–593 (1987).

Kreider et al., "Morphological Transformation In vivo of Human Uterine Cervix with Papillomavirus from Condylomata acuminata," *Nature*, 317:639–641 (1985).

(List continued on next page.)

*Primary Examiner*—Mary E. Mosher
*Attorney, Agent, or Firm*—Nixon Peabody LLP

[57] ABSTRACT

The present invention is directed to a method of expressing the papillomavirus capsid protein coding sequence in a cell using an expression system under conditions facilitating expression of the protein in the cell. In another aspect of the invention, it has been discovered that virus-like particle(s) (VLPs), fragment(s), capsomer(s) or portion(s) thereof are formed from the papillomavirus capsid protein. It was further discovered that the virus-like particle(s) comprises antigenic characteristics similar to those of native infectious papillomavirus particles. In one embodiment of the invention, there is provided a method of expressing the L1 major capsid protein of human papillomavirus type-6 (HPV-6) and type-11 (HPV-11) in Sf-9 insect cells using the baculovirus expression system, and the production of type 6 (HPV-6), type-11 (HPV-11), type-16 (HPV-16) and type-18 (HPV-18) virus-like particles. In yet another embodiment, the invention provides a method of vaccinating a mammal for papillomavirus by administering papillomavirus virus-like particles orally to a mammal in an amount sufficient to induce an immune response to the papillomavirus.

6 Claims, 18 Drawing Sheets

OTHER PUBLICATIONS

Zhou et al., "Expression of Vaccinia Recombinant HPV 16 L1 and L2 ORF Proteins in Epithelial Cells is Sufficient for Assembly of HPV Viron–like Particles," *Virology*, 185:251–257 (1991).

Biberstein, "Immunization Therapy of Warts," *Arch. Dermatol Syphilol*, 50:12–22 (1944).

Powell et al., "Treatment of Condyloma acuminata by Autogenous Vaccine," *South Med. J.*, 63:202–205 (1970).

Malison et al., "Autogenous Vaccine Therapy for Condyloma acuminatum: A Double–Blind Controlled Study," *Br. J. Vener. Dis.*, 58:62–65 (1982).

Gissmann et al., "Human Papillomaviruses and Cervical Cancer," *Cancer Cells*, 5:275–280 (1987).

Bonnez et al., "Use of Human Papillomavirus Type 11 Virions in an Elisa to Detect Specific Antibodies in Humans with Condylomata acuminata," *J. Gen. Virol.*, 72:1343–1347 (1991).

Rose et al., "Expression of the Full–Length Products of the Human Papillomavirus Type 6b (HPV–6b) and HPV–11 L2 Open Reading Frames by Recombinant Baculovirus, and Antigenic Comparisons with HPV–11 Whole Virus Particles," *J. Gen. Virol.*, 71:2725–2729 (1990).

Bonnez et al., "Antibody–Mediated Neutralization of Human Papillomavirus Type 11 (HPV–11) Infection in the Nude Mouse: Detection of HPV–11 mRNAs," *J. Inf. Dis.*, 165:376–380 (1992).

Summers et al., "A Manual of Methods for Baculovirus Vectors and Insect Cell Culture Procedures," Texas A&M University College Station, Texas (1987).

Laemmli, "Cleavage of Structural Proteins During the Assembly of the Head of Bacteriophage T4," *Nature*, 227:680–685 (1970).

Stoscheck, "Quantitation of Protein," Abelson, eds., *Methods in Enzymology*, vol. 182, New York, New York:Academic Press, Inc., pp. 50–68 (1990).

Stanley et al., "Construction of a New Family of High Efficiency Bacterial Expression Vectors: Identification of cDNA Clones Coding for Human Liver Proteins," *The EMBO J.*, 3(6):1429–1434 (1984).

Klug et al., "Structure of Viruses of the Papilloma–polyoma Type I. Human Wart Virus," *J. Mol. Biol.*, 11:403–423 (1965).

Bonnez et al., "Evolution of the Antibody Response to Human Papillomavirus Type 11 (HPV–11) in Patients with Condyloma Acuminatum According to Treatment Response," *J. Med. Virol.*, 39:340–344 (1993).

Christensen et al., "Detection of Human Serum Antibodies that Neutralize Infectious Human Papillomavirus Type 11 Virions," *J. Gen. Virol.*, 73:1261–1267 (1992).

Christensen et al., "Antibody–Mediated Neutralization In vivo of Infectious Papillomaviruses," *J. Virol.*, 64(7):3151–3156 (1990).

Shaw et al., "A Conserved AU Sequence from the 3' Untranslated Region of GM–CSF mRNA Mediates Selective mRNA Degradation," *Cell*, 46:659–667 (1986).

Cole et al., "cis–Acting Determinants of c–myc mRNA Stability," *Enzyme*, 44:167–180 (1990).

Shyu et al., "Two Distinct Destabilizing Elements in the c–fos Message Trigger Deadenylation as a First Step in Rapid mRNA Decay," *Genes & Development*, 5:221–231 (1991).

Savant–Bhonsale et al., "Evidence for Instability of mRNAs Containing AUUUA Motifs Mediated Through Translation–Dependent Assembly of a > 20S Degradation Complex," *Genes & Development*, 6:1927–1939 (1992).

Kirnbauer et al., "Papillomavirus L1 Major Capsid Protein Self–Assembles Into Virus–like Particles that are Highly Immunogenic," *Proc. Natl. Acad. Sci. USA*, 89:12180–12184 (1992).

Carter et al., Expression of Human Papillomavirus Proteins in Yeast *Saccharomyces cerevisiae*, *Virology*, 182:513–521 (1991).

Karasuyama et al., Establishment of Mouse Cell Lines Which Constitutively Secrete Large Quantities of Interleukin 2, 3, 4 or 5, Using Modified cDNA Expression Vectors, *Eur. J. Immunol.* 18:97–104 (1988).

Xi et al., "Baculovirus Expression of the Human Papillomavirus Type 16 Capsid Proteins: Detection of L1–L2 Protein Complexes," *J. Gen Virology*, 72:2981–2988 (1991).

Hagensee et al., "Self–Assembly of Human Papillomavirus Type 1 Capsids by Expression of the L1 Protein Alone or by Coexpression of the L1 and L2 Capsid Proteins," *J. of Virology*, 67(1):315–322 (1993).

Rose et al., "Expression of Human Papillomavirus Type 11 L1 Protein in Insect Cells: In Vivo and In Vitro Assembly of Viruslike Particles," *J. of Virology*, 67(4):1936–1944 (1993).

Rose et al., "Serological Differentiation of Human Papillomavirus Types 11, 16, and 18 Using Recombinant Virus–Like Particles," *J. of Gen Virology*, 75:2445–2449 (1994).

Rose et al., "Human Papillomavirus Type 11 (HPV–11) Virus–Like Particles (VLPs) Induce the Formation of Neutralizing Antibodies," $12^{th}$ International Papillomavirus Conference, Sep.–Oct. 1993 (abstract).

Kirnbauer et al., "Efficient Self–Assembly of Human Papillomavirus Type 16 L1 and L1–L2 into Virus–Like Particles," *J. Virol.* 67(12):6929–6936 (1993).

Ghim et al., "HPV–1 L1 Protein Expressed in cos Cells Displays Conformational Epitopes Found on Intact Virions," *Virology*, 190:548–552 (1992).

Browne et al., "Analysis of the L1 Gene Product of Human Papillomavirus Type 16 by Expression in a Vaccinia Virus Recombinant," *J. Gen. Virol.*, 69:1263–1273 (1988).

U.S. Patent Application Serial No. 07/941,371 filed Sep. 3, 1992.

O'Neal et al., "Rotavirus Virus–Like Particles Administered Mucosally Induce Protective Immunity," *Journal of Virology*, 71(11):8707–8717 (1997).

Ball et al., "Oral Immunization with Recombinant Norwalk Virus–Like Particles Induces a Systemic and Mucosal Immune Response in Mice," *Journal of Virology*, 72(2):1345–1353 (1998).

Suzich, J.A. et al. Proceedings of the National Academy of Sciences USA 92:11553–116557, Dec. 1995.

Lowe, R.S. et al. Journal of Infectious Diseases 176:1141–1145, 1997.

Jansen, K.U. et al. Vaccine 18:1509–1514, 1995.

Kirnbauer, R. et al. Virology 219:37–44, 1996.

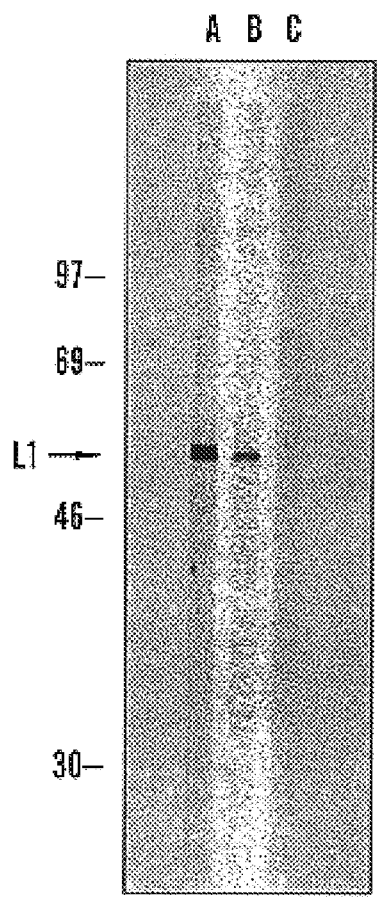
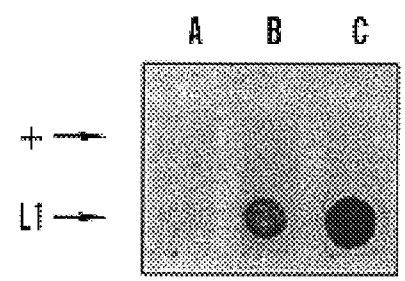
*FIG. 3B*
*FIG. 3A*

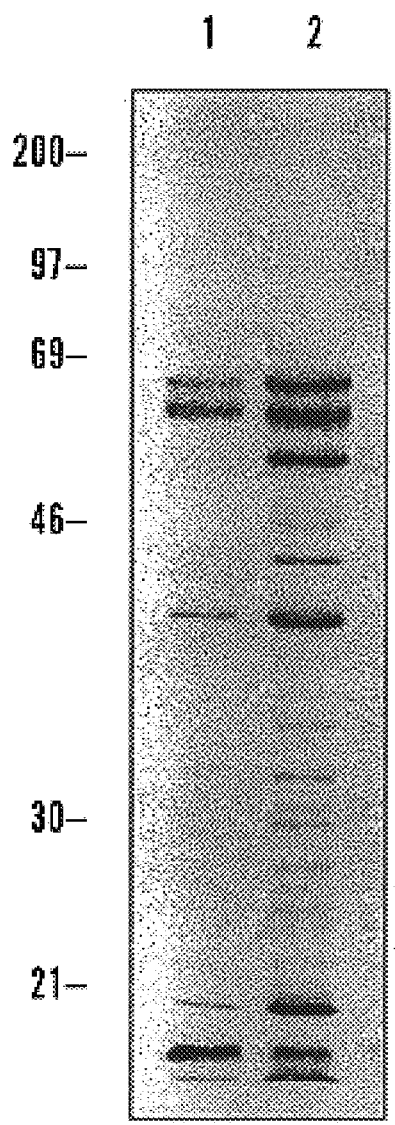 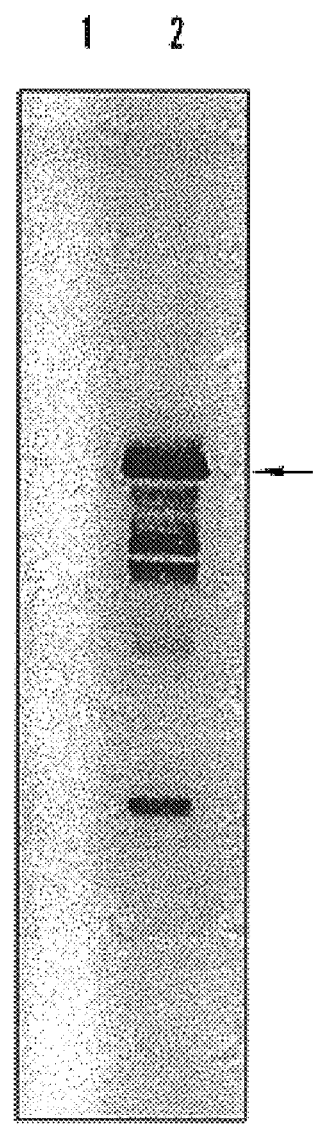
*FIG. 11A*  *FIG. 11B*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

CGCAGATCTA TGTGGCGGCC TAGC                                         24

(2) INFORMATION FOR SEQ ID NO:2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CATATGAATT CCCACAACAC ACTGACACAC                                   30

ORAL IMMUNIZATION WITH PAPILLOMAVIRUS VIRUS-LIKE PARTICLES

The present application is a continuation-in-part of U.S. patent application Ser. No. 08/207,309, filed Mar. 7, 1994, now pending, which is a continuation-in-part of U.S. patent application Ser. No. 08/028,517, filed Mar. 9, 1993, now pending.

The United States Government may have certain rights in this invention pursuant to Public Health Service awards AI-82509, AI-35159 and CA-11198 from the National Institutes of Health.

FIELD OF THE INVENTION

The present invention relates generally to papillomavirus (PV). More particularly, the invention relates to a method of expressing the human papillomavirus type 6 (HPV-6) and type 11 (HPV-11) capsid protein coding sequence using the baculovirus expression system, production of HPV virus-like particles (VLPS) and use of these VLPs in production of antibodies which recognize epitopes on HPV, and for HPV vaccine development, and for development of serologic tests for the detection of HPV infection.

BACKGROUND OF THE INVENTION

The family Papovaviridae constitutes a group of DNA viruses that induce both lytic infections and either benign or malignant tumors. Structurally, all are naked icosahedral virions with 72 capsomeres and contain double-stranded circular DNA. Viruses included in the family are: (1) human and animal papillomaviruses, (2) mouse polyomavirus, (3) simian vacuolating virus, and (4) human viruses BK and JC.

Human papillomaviruses (HPV) infect cutaneous, genital, oral, and respiratory epithelia in a tissue-specific manner. Infection with HPV has been associated closely with the development of both benign lesions and malignancies (Reichman et al., *Papillomaviruses*, 1990, pp. 1191–1200; and Mandell et al., *Principles and Practice of Infectious Diseases*, 3rd Edition, Churchill Livingstone, New York, N.Y.). For example, HPV type 1 (HPV-1) is present in plantar warts, HPV types 6 or 11 (HPV-6 or HPV-11) in condylomata acuminata (anogenital warts), while HPV types 16 or 18 (HPV-16 or HPV-18) are common in premalignant and malignant lesions of the cervical squamous epithelium (See Crum et al., "Human papillomavirus infection and cervical neoplasia: New perspectives," *Int. J. Gynecol. Pathol.* 3:376–388 (1984); zur Hausen, *Genital Papillomavirus Infections*, 1985, pp. 83–90; Rigby et al., *Viruses and Cancer*, Cambridge University Press, Cambridge, UK; and Koutsky et al., "Epidemiology of genital human papillomavirus infection," *Epidemiol. Rev.* 10:122–163 (1988)).

However, difficulties in propagating HPV in vitro has led to the development of alternative approaches to antigen production for immunologic studies. For example, Bonnez et al., "The PstI-XhoII restriction fragment of the HPV-6b L1 ORF lacks immunological specificity as determined by sera from HPV 6 condyloma acuminatum patients and controls," *UCLA Symp. Mol. Cell. Biol.*, New Series, 124:77–80 (1990); Jenison et al., "Identification of immunoreactive antigens of human papillomavirus type 6b by using *Escherichia coli*-expressed fusion proteins," *J. Virol.* 62:2115–2123 (1988); Li et al., "Identification of the human papillomavirus type 6b L1 open reading frame protein in condylomas and corresponding antibodies in human sera," *J. Virol.* 61:2684–2690 (1987); Steele et al., "Humoral assays of human sera to disrupted and nondisrupted epitopes of human papillomavirus type 1," *Virology* 174:388–398 (1990); and Strike et al., "Expression in *Escherichia coli* of seven DNA segments comprising the complete L1 and L2 open reading frames of human papillomavirus type 6b and the location of the 'common antigen'," *J. Gen. Virol.* 70:543–555 (1989), have expressed recombinant capsid protein coding sequences in prokaryotic systems, and used them in Western blot analyses of sera obtained from individuals with HPV infection of the genital tract. Results from these studies have suggested that antibodies to denatured, i.e. linear, epitopes of HPV capsid proteins can be detected in the sera of some infected individuals.

Whole virus particles have also been used to detect antibodies in human sera, including antibodies directed against conformational epitopes. These studies have been difficult to conduct because most naturally occurring HPV-induced lesions produce few particles. Whole virus particles can be obtained, however, in amounts sufficient to conduct immunologic assays from HPV type 1-induced plantar warts (Kienzler et al., "Humoral and cell-mediated immunity to human papillomavirus type 1 (HPV-1) in human warts," *Br. J. Dermatol.* 108:65–672 (1983); "Pfister et al., Seroepidemiological studies of human papilloma virus (HPV-1) infections," *Int. J. Cancer* 21:161–165 (1978); and Steele et al., "Humoral assays of human sera to disrupted and non-disrupted epitopes of human papillomavirus type 1," *Virology* 174:388–398 (1992)) and experimentally-induced HPV-11 athymic mouse xenographs (Kreider et al., "Laboratory production in vivo of infectious human papillomavirus type 11," *J. Virol.* 61:590–593 (1991); and Kreider et al., "Morphological transformation in vivo of human uterine cervix with papillomavirus from condylomata acuminata," *Nature* 317:639–641 (1985)). More particularly, U.S. Pat. No. 5,071,757 to Kreider et al., discloses a method of propagating infectious HPV-11 virions in the laboratory using an athymic mouse xenograph model system. Although this system is capable of producing quantities of infectious virus that could be used for the development of a serologic test for genital HPV infection, this system is very expensive and cumbersome. Furthermore, only one genital HPV type has so far been propagated in this system, thus, limiting its usefulness. In addition, the infectious virus produced using this system represents a biohazard and, therefore, would be difficult to use in a vaccine formulation.

Zhou et al., in "Expression of vaccinia recombinant HPV 16 L1 and L2 ORF proteins in epithelial cells is sufficient for assembly of HPV virion-like particles", *Virology* 185:251–257 (1992), have reported the formation of HPV-16 virus-like particles in CV-1 cell nuclei following infection with a vaccinia virus HPV-16 L1/L2 double recombinant expression vector. However, the authors were not able to produce VLPs with a vector expressing L1 alone. Furthermore, the VLPs produced lacked a well-defined symmetry, and were more variable in size and smaller, only about 35–40 nm in diameter, than either HPV virions (55 nm) or the VLPs of the present invention (baculovirus produced HPV-11 VLPs, about 50 nm in diameter).

U.S. Pat. No. 5,045,447, to Minson, discloses a method of screening hybridoma culture supernatants for monoclonal antibodies with desired specificities. Minson's method is exemplified by the production of antibodies to the L1 protein of human papillomavirus type 16 (HPV-16) using this protein as the target antigen in mice. However, Minson fails to disclose the expression of the L1 protein or production of HPV virus-like particles (VLPs).

U.S. Pat. No. 4,777,239, to Schoolnik et al., discloses short peptide sequences derived from several of the papillomavirus early region open reading frames which elicit type-specific antibodies to papillomavirus. However, the inventors fail to disclose any sequences directed to the major late open reading frame, L1.

U.S. Pat. No. 5,057,411 to Lancaster et al., discloses a polynucleotide sequence of about 30 nucleotides of the papillomavirus L1 capsid protein open reading frame that the inventors contend encode a papillomavirus type-specific epitope. However, the inventors do not disclose infected animals that produced antibodies which recognize this sequence. Instead, they synthesized a bovine papillomavirus type 1 (BPV-1) version of the sequence (a 10 amino acid peptide, or decapeptide), then immunized rabbits and tested the antiserum's ability to react with either BPV-1 or BPV-2 induced fibropapilloma tissue. The peptide antiserum only reacted with BPV-1 and not BPV-2 tissue. The inventors then concluded that the peptide contained an antigenic determinant that was type-specific, and therefore, all papillomavirus L1 coding sequences contain a type-specific epitope at this locus. This is theoretical speculation on the part of the inventors, who give no supporting data for this hypothesis. In addition, the amino acid sequences disclosed (10 amino acids) are generally thought not to be capable of adopting higher order antigenic structures, i.e., conformational epitopes that possess a three-dimensional structure such as those produced by the method described herein.

Another problem associated with papillomavirus infections is the need for alternative therapeutic and prophylactic modalities. One such modality which has received little recent study, would be papillomavirus vaccines. In 1944, Biberstein treated condyloma acuminatum patients with an autogenous vaccine derived from the patients' warts (Biberstein, "Immunization therapy of warts," *Arch. Dermatol Syphilol.* 50:12–22 (1944)). Thereafter, Powell et al., developed the technique typically used today for preparing autogenous wart vaccines for the treatment of condyloma acuminatum (Powell et al., "Treatment of condylomata acuminata by autogenous vaccine," *South Med. J.* 63:202–205 (1970)). Only one double-blind, placebo-controlled study has attempted to evaluate the efficacy of the autogenous vaccine (Malison et al., "Autogenous vaccine therapy for condyloma acuminatum: A double-blind controlled study," *Br. J. Vener. Dis.* 58:62–65 (1982)). The authors concluded that autogenous vaccination was not effective in the treatment of condylomata acuminata, although this interpretation may be erroneous. The small number of patients studied precluded drawing valid negative conclusions. In any event, autogenous vaccines, as presently described, have several disadvantages. First, the patient needs to have relatively large warts (2 g to 5 g) in order to prepare the vaccine. Secondly, the practitioner needs access to laboratory equipment and expertise each time a new patient is to be treated. Thus, vaccine preparation is very expensive, tedious, and in cases involving relatively small lesion mass, not possible.

Unfortunately, traditional methods of virus propagation have not yet been adapted to the study of papillomaviruses, and the alternative methods previously described fail to produce infectious virions in any significant amounts for immunologic studies. Also, in vivo propagation of HPV-11 in the athymic mouse system is not very practical because it is expensive, labor intensive and currently limited to HPV-11. Consequently, an alternative method of producing epitopes of HPV capsid for use in immunologic studies and vaccine production is needed.

SUMMARY OF THE INVENTION

The present invention is directed to a method of expressing the capsid protein coding sequence of papillomavirus (PV) in a cell, comprising transfecting the cell with an expression vector containing the papillomavirus capsid protein coding sequence under conditions facilitating expression of the protein in the cell.

In another aspect of the invention, there is provided a virus-like particle(s) (VLPs), fragment(s), capsomer(s) or portion(s) thereof, formed from papillomavirus capsid protein. It has been discovered that the virus-like particle(s) comprises antigenic characteristic(s) similar to those of native infectious papillomavirus particles.

In a preferred embodiment of the invention, there is provided a method of expressing the L1 capsid protein coding sequence of human papillomavirus type-6 (HPV-6) and type-11 (HPV-11) in Sf-9 insect cells using the baculovirus expression system. The HPV-6 and HPV-11 coding sequences were cloned using standard techniques in the art into a baculovirus transfer vector. The resulting baculovirus transfer vector were used to co-transfect Sf-9 insect cells with *Autographa californica* nuclear polyhedrosis virus (AcNPV) forming a recombinant baculovirus (Ac6L1 or Ac11L1) which was recovered. Sf-9 insect cells were thereafter infected with either Ac6L1 or Ac11L1 under conditions facilitating expression of the protein in the cells. It was discovered that the L1 protein formed virus-like particles (VLPs). VLPs were identified by electron microscopy of negatively-stained sucrose band fractions obtained from Sf-9 cells infected with the Ac11L1 recombinant baculovirus. It was further discovered that the VLPs possessed immunological and morphological characteristics similar to those of native HPV-11 virions, as defined by rabbit antisera.

Virus-like particle(s) produced in accordance with the invention, can be used in diagnostic assays, can play a role in the identification and characterization of an HPV cell receptor, and can be used for vaccine development (both therapeutic and prophylactic). It is understood that the method of the invention as described herein for production of HPV-11 and HPV-6 can be used to produce similar immunologic reagents from other animal and/or human papillomaviruses. In addition, VLPs produced in accordance with the invention will provide abundant reagents with which to carry out immunologic studies of papillomaviruses and for developing vaccines against papillomaviruses.

The present invention also provides a method of vaccinating a mammal against papillomavirus infection by administering papillomavirus virus-like particles orally to a mammal in an amount sufficient to induce an immune response to the papillomavirus.

BRIEF DESCRIPTION OF THE FIGURES

FIG. 3 shows Western blot and immunodotblot comparisons of rabbit antisera immunoreactivities with recombinant L1. In panel A, recombinant L1 insect cell lysate was Western blotted under denaturing conditions. In panel B, non-recombinant (+) or recombinant L1 (L1) insect cell lysates were applied to a blotting membrane under non-denaturing conditions. Strips A were probed with a rabbit polyclonal antiserum specific for the HPV L1 common epitope; strips B were probed with a rabbit polyclonal antiserum specific for the amino-terminal amino acid sequence of HPV L1; strips C were probed with a rabbit polyclonal whole virus particle antiserum.

FIG. 11 shows SDS Page and Western immunoblot detection of recombinant HPV-11 L1 in the Ac11L1-infected Sf-9 cell culture supernatant. FIG. 11A shows a SDS polyacrylamide gel (Coomassie stained). FIG. 11B is a western blot, using the PVL1 common antigen serum; Lane 1: High speed pellet from non-recombinant AcNPV-infected cell culture supernatant; Lane 2: High-speed pellet from Ac11L1-infected Sf-9 cell culture supernatant; Molecular weight markers ($M_r$) are at the left; Arrow at the right denotes the position of 55 kD $M_r$ recombinant L1).

FIG. 20 (A–B) depicts a VLP Binding Inhibition (VBI) ELISA. Monoclonal and polyclonal HPV-11 virus-neutralizing antibodies, and orally induced murine HPV-11 VLP polyclonal antibodies, were evaluated in an HPV-11 VLP ELISA.

DETAILED DESCRIPTION OF THE INVENTION

Figure 1A:
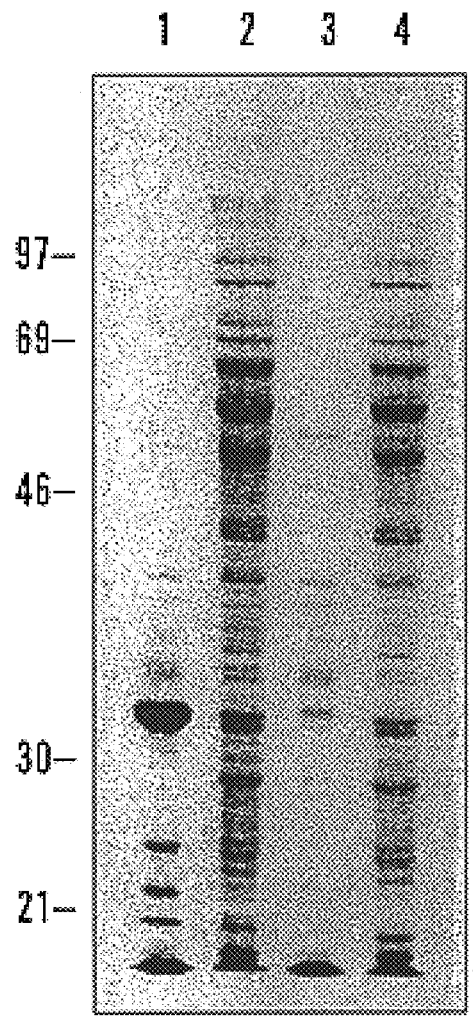
FIG. 1A shows Coomassie-blue stained SDS polyacrylamide gel of wild-type AcNPV and recombinant Ac11L1-infected SF-9 cell lysates.

The present invention is directed to a method of expressing the papillomavirus capsid protein coding sequence in a cell using the baculovirus expression system under conditions facilitating expression of the protein in the cell. In another aspect of the invention, it has been discovered that virus-like particle(s) (VLPs), fragment(s), capsomer(s) or portion(s) thereof are formed from the papillomavirus capsid protein. It was further discovered that the virus-like particle (s) comprises antigenic characteristics similar to those of native infectious papillomavirus particles.

As used herein, "virus-like particle(s) (VLPs)" refer to a virus-like particle(s), fragment(s), capsomer(s) or portion(s) thereof produced from the capsid protein coding sequence of papillomavirus and comprising antigenic characteristic(s) similar to those of infectious papillomavirus particles. As used herein, "antigenic characteristic(s)" refers to (1) the ability of the virus-like particle(s) to cross-react with wild-type particles (native infectious virus particles of the same HPV type) as determined by antisera generated in animals and/or humans by immunization with either VLPs or infectious virus; and/or (2) the ability to recognize or detect antibodies in human sera from persons known to be infected with homologous virus.

As used herein, "L1 protein coding sequence" or "L1 capsid protein coding sequence" or "L1 coding sequence" refers to the open reading frame which codes for the L1 protein in papillomavirus. When expressed, the L1 protein coding sequence produces a protein, or protein complex, or aggregate, which possesses immunological and morphological characteristics similar to those of native papillomavirus virions. The L1 coding sequence used in the invention can be isolated and purified from papillomavirus genomic DNA or synthesized using standard genetic engineering techniques.

As used herein, the term "transfecting" refers to any means for introducing a virus, plasmid or vector into a cell. Examples of such means include infection, calcium phosphate precipitation and electroporation.

In a preferred embodiment of the invention, there is provided a method of expressing the coding sequence for the L1 capsid protein of human papillomavirus type-11 (HPV-11) or human papillomavirus type-6 (HPV-6) in Sf-9 insect cells using the baculovirus expression system. It is understood that the capsid protein coding sequences of these HPV types are used for purposes of illustration only, and that any L1 capsid protein coding sequence for any animal or human papillomavirus type can be used without deviating from the intended scope of the invention. Such HPV types include, without limitation, HPV types 16, 18, 31, 33, 35 (Gissman et al., *Cancer Cells* 5:275 (1987), which is hereby incorporated by reference); and those HPV types disclosed in PCT publication no. WO 92/16636 to Boursnell et al., which is hereby incorporated by reference.

The preferred expression system used in the method of the invention is the baculovirus expression system, however, it is understood that any other expression system(s) can be employed herein provided the system(s) can express the L1 protein coding sequence. Examples of such systems include, without limitation, any prokaryotic and/or eukaryotic system (s) including adenovirus, SV40, *E. coli*, CHO cells, vaccinia virus, insect viruses, yeast, bacteriophage virus or modified viruses, DNA plasmids, vectors and the like.

The host cell for expression of the L1 coding sequence is dependent on the expression system used. Examples of suitable host cells include, without limitation, bacteria (prokaryotic), microorganisms such as yeast, mammalian cells (eukaryotic) and insect cells. When using the baculovirus expression system. insect cells, such as Sf-9 or Sf-21 are preferred.

In another aspect of the invention, it was discovered that the L1 protein produces virus-like particles (VLPs), fragment(s), capsomer(s) or portion(s) thereof, formed from papillomavirus capsid protein. It has been discovered that the virus-like particle(s) comprises antigenic characteristic (s) similar to those of native infectious papillomavirus particles. More particularly, these VLPs contain an antigenic determinant that is specifically recognized by antibodies present in sera obtained from genital HPV-infected patients. For example, reaction of VLP-containing insect cell extracts with antisera directed against either denatured or non-denatured capsid epitopes, as deduced by immunoreactivities in Western blot and immunodotblot assays, suggested that conformational epitopes present in native HPV-11 infectious virions were also present on the baculovirus-produced HPV-11 VLPs of the present invention. Immunodotblot assays using human sera obtained from individuals with biopsy proven condylomata acuminatum correlated closely with results previously obtained in HPV-11 whole virus particle-based ELISA tests as described by Bonnez et al., "Use of human papillomavirus type 11 virions in an ELISA to detect specific antibodies in humans with condylomata acuminata," *J. Gen. Virol.* 72:1343–1347 (1991), which is hereby incorporated by reference.

These morphologic and immunologic similarities to native HPV-11 virions suggest that recombinant VLPs produced in the baculovirus system will be useful in sero-epidemiology and pathogenesis studies of not only genital HPV infection but for any papillomavirus and for vaccine development. L1 has an intrinsic capacity for self-assembly. Thus, other papillomavirus proteins are not required for VLP formation in the baculovirus system. This supports the contention that VLPs to all types of papillomaviruses can be produced in accordance with the method described herein.

The VLPs of the invention can be used to raise antibodies, either in subjects for which protection against infection by HPV is desired, i.e., vaccines, or to heighten the immune response to an HPV infection already present. The VLPs of the invention can be injected into animal species to obtain antisera useful in diagnosis. In addition to polyclonal antisera, monoclonal antibodies can be obtained using the methods of Kohler and Milstein, or by modifications thereof, by immortalizing spleen or other antibody-producing cells from injected animals to obtain antibody-producing clones, i.e., hybridomas.

The antibodies obtained can be used for diagnosis of HPV infection in cervical biopsies or Papanicolaou smears and in assessing disease levels in humans or other subjects. In particular, diagnosis using the antibodies of the invention permits monitoring the evolution of the disease. The antibodies can be used in analysis of serum to detect the virus, as well as to monitor the progress of therapy with antiviral or other therapeutic agents directed to control of the infection or carcinoma. The antibodies can also be used as passive therapy, taking into account species variations.

The VLPs of the invention can be used in immunoassays to detect the presence of antibodies raised against HPV in the serum of patients suspected of harboring HPV infections or to titrate the sera of patients being treated with an anti-HPV vaccine.

The VLPs of the invention can be directly administered to a host to induce the formation of neutralizing antibodies (Bonnez et al., "Antibody-mediated neutralization of human papillomavirus type 11 (HPV-11) infection in the nude mouse: Detection of HPV-11 mRNAs by the polymerase chain reaction," *J. Inf. Dis.*, 165: 376–380 (1992); Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which are hereby incorporated by reference), to confer either protective immunity against HPV or, if the patient is already infected, to boost the patient's own immune response. For all applications, the VLPs are administered in immunogenic form. Optionally, the VLPs can be conjugated to an immunogenicity conferring carrier material, the material preferably being antigenically neutral. Depending on the use required, the VLPs of the invention have the ability to serve as type specific or broad range vaccines and diagnostics.

VLPs which are to be administered as vaccines can be formulated according to conventional and/or future methods for such administration to the subject to be protected and can be mixed with conventional adjuvants. The peptide expressed can be used as an immunogen in subunit vaccine formulations, which may be multivalent. The multivalent vaccine formulation can comprise VLPs each encoding a different L1 protein from different HPVs. The product may be purified for purposes of vaccine formulation from any vector/host systems that express the heterologous protein. The purified VLPs should be adjusted to an appropriate concentration, formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides; oil emulsions; and potentially useful human adjuvants such as BCG (Bacille Calmette-Guerin) and *Corynebacterium parvum*. The immunogen may also be incorporated into liposomes, or conjugated to polysaccharides and/or other polymers for use in a vaccine formulation. Many methods may be used to introduce the vaccine formulations described above; these include, but are not limited to, oral, intradermal, intramuscular, intraperitoneal, intravenous, subcutaneous and intranasal routes. If they are to be used directly, as diagnostic reagents, they are purified using conventional methods and packaged accordingly for such use. If they are to be used to produce antibodies for diagnostic purposes, convenient test animals can be used to prepare the appropriate antisera. Suitable hosts include mice, rats, rabbits, guinea pigs, or even larger mammals such as sheep. The antibodies can be used therapeutically so long as they are compatible with the host to be treated. Monoclonal antibodies having the proper species characteristics are preferred for this application.

In a preferred embodiment, the invention provides a method of vaccinating a mammal for papillomavirus by administering papillomavirus virus-like particles orally to a mammal in an amount sufficient to induce an immune response to the papillomavirus. In order to obtain a high degree of protection, the method may also involve administering one or more vaccine booster inoculations of papillomavirus virus-like particles orally to the mammal. In a preferred embodiment of the invention, the immune response induced by oral immunization will protect the mammal from infection by papillomavirus.

The preferred papillomavirus is a human papillomavirus, in particular Human Papillomavirus Type 6 and Type 11.

The present invention also provides oral vaccines having papillomavirus virus-like particles and a pharmaceutically acceptable carrier. Oral vaccines may also include flavorings, colorings, and other food additives to make the vaccine more palatable. In addition, oral vaccines may also contain stabilizers and preservatives to extend the shelf life of the vaccine.

Prophylactic vaccination with recombinant VLPs has emerged as a strategy for the prevention of anogenital HPV infection (Kimbauer, R., "Papillomavirus-Like Particles For Serology and Vaccine Development," *Intervirology* 39(1–2):54–61 (1996); Rose, R. C., et al., "Human Papillomavirus Infections," p. 343–368. In G. J. Galasso, R. J. Whitley, and T. C. Merigan (eds.), "Antiviral Agents and Human Viral Diseases," 4$^{th}$ ed. Lippincott-Raven Publishers, Philadelphia (1997); Schiller, J. T., et al., "Papillomavirus-Like Particles and hpv Vaccine Development," *Seminars in Cancer Biology* 7(6):373–382 (1996), which are hereby incorporated by reference). VLPs are highly immunogenic when administered parenterally (Kimbauer, R. F., et al., "Papillomavirus L1 Major Capsid Protein Self-Assembles into Virus-Like Particles That Are Highly Immunogenic," *Proceedings of the National Academy of Sciences of the United States of America* 89(24):12180–12184 (1992); Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which are hereby incorporated by reference), and have been shown to elicit protective immune responses (Breitburd, F., et al., "Immunization With Virus-Like Particles From Cottontail Rabbit Papillomavirus (CRPV) Can Protect Against Experimental CRPV Infection," *J. Virology* 69(6):3959–3963 (1995); Christensen, N. D., et al., "Assembled Baculovirus-Expressed Human Papillomavirus Type 11 L1 Capsid Protein Virus-Like Particles Are Recognized By Neutralizing Monoclonal Antibodies and Induce High Titres of Neutralizing Antibodies," *J. Gen. Virol.* 75:2271–2276 (1994); Kimbauer, R., et al., "Virus-Like Particles of Bovine Papillomavirus Type 4 in Prophylactic and Therapeutic Immunization," *Virology* 219(1):37–44 (1996); Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994); Suzich, J. A., et al., "Systemic Immunization With Papillomavirus L1 Protein Completely Prevents the Development of Viral Mucosal Papillomas," *Proc. Natl. Acad. Sci.*, USA 92:11553–11557 (1995); White, W. I., et al., "In Vitro Infection and Type-Restricted Antibody-Mediated Neutralization of Authentic Human Papillomavirus Type 16," *J. Virology* 72:959–964 (1998), which are hereby incorporated by reference). The present results demonstrate that similar responses can be induced by oral VLP immunization. Antigenic specificities of orally induced antibodies were found to be dependent on native VLP structure, and restricted according to HPV genotype. Results from the epitope-blocking ELISA indicated that post-immune serum antibodies efficiently inhibited VLP binding by HPV-11 virus-neutralizing antibodies. The detection of antigen structure-dependent antibody specificities in the murine post-immune sera indicated that HPV-11 VLPs maintained their native structure and antigenicity despite acid pH in the stomach and abundant proteases in the small intestine. This demonstrates the usefulness of VLPs as oral immunogens for the prevention of anogenital HPV disease.

Oral immunization offers certain advantages over other routes of vaccination. For example, oral vaccines are more easily administered and thus may be more acceptable to vaccine recipients. Also, oral vaccines can be less pure than vaccines formulated for injection, making production costs lower. Interestingly, in some instances orally administered antigens have been shown to elicit mucosal immune responses, which may be important for protection against infection with certain pathogens (Ball, J. M., et al., "Oral Immunization With Recombinant Norwalk Virus-Like Particles Induces a Systemic and Mucosal Immune Response in Mice," *J. Virology* 72(2):1345–1353 (1998); Oneal, C. M., et al., "Rotavirus Virus-Like Particles Administered Mucosally Induce Protective Immunity," *J. Virology* 71(11):8707–8717 (1997), which are hereby incorporated by reference). Based on previous work reported by others (Kimbauer, R., et al., "Virus-Like Particles of Bovine Papillomavirus Type 4 in Prophylactic and Therapeutic Immunization," *Virology* 219 (1):37–44 (1996); Suzich, J. A., et al., "Systemic Immunization With Papillomavirus L1 Protein Completely Prevents the Development of Viral Mucosal Papillomas," *Proc. Natl. Acad. Sci.*, USA 92:11553–11557 (1995), which are hereby incorporated by reference), it was not the intent of the present study to investigate mucosal responses after oral VLP administration. However, such responses may enhance vaccine efficacy, and this possibility is now being investigated.

Intestinal antigens are believed to gain access to gut-associated lymphoid tissue (GALT) via M cells in the Peyer's Patch (PP) epithelium (Neutra, M. R., "Antigen Sampling Across Epithelial Barriers and Induction of Mucosal Immune Responses," *Annual Review of Immunology* 14:275–300 (1996), which is hereby incorporated by reference), and M-cell-mediated uptake into PP has been demonstrated for a number of microorganisms (Amerongen, H. M., et al., "Transepithelial Transport of HIV-1 By Intestinal M Cells: a Mechanism For Transmission of AIDS," *Journal of Acquired Immune Deficiency Syndromes* 4(8) :760–765 (1991); Buller, C. R., et al., "Natural Infection of Porcine Ileal Dome M Cells With Rotavirus and Enteric Adenovirus," *Vet. Pathol.* 25(6):516–517 (1988); Inman, L. R., et al., "Specific Adherence of *Escherichia Coli* (Strain RDEC-1) to Membranous (M) Cells of the Peyer's Patch in *Escherichia Coli* Diarrhea in the Rabbit," *Journal of Clinical Investigation* 71(1):1–8 (1983); Keren, D. F., et al., "The Enteric Immune Response to Shigella Antigens," *Current Topics in Microbiology & Immunology* 146:213–223 (1989); Sicinski, P., et al., Poliovirus Type 1 Enters the Human Host Through Intestinal M Cells," *Gastroenterology* 98(1):56–58 (1990); Wolf, J. L., et al., Intestinal M Cells: a Pathway for Entry of Reovirus Into the Host," *Science* 212(4493) :471–472 (1981), which are hereby incorporated by reference). M cells may be able to deliver intact VLPs directly to professional antigen presenting cells (Ball, J. M., et al., "Oral Immunization With Recombinant Norwalk Virus-Like Particles Induces a Systemic and Mucosal Immune Response in Mice," *J. Virology* 72(2):1345–1353 (1998), which is hereby incorporated by reference), which are abundant in the underlying areas of the PP (Mowat, A. M., et al., "The Anatomical Basis of Intestinal Immunity," *Immonol. Rev.* 156:145–166 (1997), which is hereby incorporated by reference). Previous work has shown that several types of antigen can elicit systemic responses after oral delivery, and that cellular binding activity may be involved in this phenomenon (de Aizpurua, H. J., et al., "Oral Vaccination. Identification of Classes of Proteins That Provoke an Immune Response Upon Oral Feeding," *J. Exp. Med.* 167(2):440–451 (1988), which is hereby incorporated by reference). It may be that the ability to bind glycolipids or glycoproteins on the intestinal mucosa may stimulate mucosal cells to transport such antigens into the circulation, thereby eliciting a systemic response (de Aizpurua, H. J., et al., "Oral Vaccination. Identification of Classes of Proteins That Provoke an Immune Response Upon Oral Feeding," *J. Exp. Med.* 167(2):440–451 (1988), which is hereby incorporated by reference). Papillomavirus VLPs bind to a variety of eukaryotic cell types (Müller, M., et al., "Papillomavirus Capsid Binding and Uptake by Cells From Different Tissues and Species," *J. Virology* 69(2):948–954 (1995); Volpers, C., et al., "Binding and Internalization of Human Papillomavirus Type 33 Virus-Like Particles by Eukaryotic Cells," *J. Virology* 69(6):3258–3264 (1995), which are hereby incorporated by reference), and this ability may be involved in the induction of responses such as those described in the present study. Although natural infection by papillomaviruses is thought to be receptor-mediated, a role for a specific receptor in the induction of immune responses after oral vaccination is unlikely, as papillomaviruses are not known to infect intestinal mucosal epithelial tissues, and mice are not naturally susceptible to HPV infection.

Results obtained in the epitope-blocking ELISA indicate that orally induced antibodies efficiently block VLP binding by HPV-11 virion neutralizing antibodies. Native virions are costly to produce (Bonnez, W., et al., "Propagation of Human Papillomavirus Type 11 in Human Xenografts Using the Severe Combined Immunodeficiency (SCID) Mouse and Comparison to the Nude Mouse Model," *Virology* 197(1) :455–458 (1993); Kreider, J. W., et al., "Laboratory Production in vivo of Infectious Human Papillomavirus Type 11," *J. Virology* 61:590–593 (1987), which are hereby incorporated by reference), and are not available for most clinically relevant virus genotypes. Therefore, the epitope-blocking ELISA is a useful alternative to virion infectivity assays for predicting vaccine efficacy. It may also be more reliable than other recently described surrogate assays. For example, a hemagglutination inhibition assay (HAI) (Roden, R. B., et al., "Assessment of the Serological Relatedness of Genital Human Papillomaviruses by Hemagglutination Inhibition," *J. Virology* 70(5):3298–3301 (1996), which is hereby incorporated by reference), which suggests the possibility that the mechanism(s) by which antibodies neutralize infectious HPV virions may differ from the mechanism(s) involved in VLP-mediated hemagglutination. By contrast, results from the epitope-blocking ELISA indicated the presence of H11.H3 neutralizing antigenic specificity in rabbit HPV-11 N-pAb, and thus indicated indirectly the presence of the same specificity in antibodies induced after oral immunization.

Roughly 450,000 new cases of invasive uterine cervical carcinoma are diagnosed annually worldwide (Munos, N., "Disease-Burden Related to Cancer Induced by Viruses and H.pylori," *World Health Organization (WHO) Vaccine Research and Development: Report of the Technical Review Group Meeting* Jun. 9–10, 1997 (1997), which is hereby incorporated by reference). Therefore, efficient methods of vaccine delivery will be needed for the immunization of large numbers of susceptible individuals. Thus, oral immunization strategies will certainly facilitate implementation of mass immunization programs designed to reduce the incidence of cervical cancer and other HPV-associated diseases.

The following Examples are provided to further illustrate the present invention.

EXAMPLE I

Methods

1. HPV-11 Viral DNA And pVL11L1 Baculovirus Transfer Vector Construction.

HPV-11 genomic DNA was obtained from virus particles which were purified from experimentally induced athymic mouse xenografts as described by Rose et al., "Expression of the full-length products of the HPV-6b and HPV-11 L2 open reading frames by recombinant baculovirus, and antigenic comparisons with HPV-11 whole virus particles," *J. Gen. Virol.* 71:2725–2729 (1990), which is hereby incorporated by reference. The L1 coding sequence was cloned by PCR amplification of purified genomic DNA, using primers designed to introduce BglII and EcoRl restriction enzyme sites at the 5' and 3' ends, respectively. The forward and reverse primer sequences, respectively, were, 5'-CGC AGA TCT ATG TGG CGG CCT AGC-3'(SEQ ID NO. 1) and 5'-CAT ATG AAT TCC CAC AAC ACA CTG ACA CAC-3' (SEQ ID NO. 2). Restriction sites (underlined) were introduced proximal to the putative L1 start codon (bold text), and approximately 30 nucleotides downstream from the putative L1 stop codon, by primer-directed mutagenesis. Amplification was performed essentially as described by Bonnez et al., "Antibody-mediated neutralization of human papillomavirus type 11 (HPV-11) infection in the nude mouse: Detection of HPV-11 mRNAs by the polymerase chain reaction," *J. Inf. Dis.*, 165: 376–380 (1992), which is hereby incorporated by reference, using 500 ng of each primer and 2 units of Taq DNA polymerase (Amplitaq, Perkin-Elmer Cetus Corp., Norwalk, Conn.). After amplification, the PCR product was digested with BglII and EcoRI. The 1539 base pair (bp) digestion product, which contained the entire HPV-11 L1 open reading frame (ORF), was purified by agarose gel electrophoresis as described by Rose et al., "Expression of the full-length products of the HPV-6b and HPV-11 L2 open reading frames by recombinant baculovirus, and antigenic comparisons with HPV-11 whole virus particles," *J. Gen. Virol.* 71:2725–2729 (1990), which is hereby incorporated by reference, and cloned into the corresponding sites of a baculovirus transfer vector, pVL-1392 (M. D. Summers, Texas A&M University, College Station, Tex.). The resulting construct, pVL11L1, was used to co-transfect Sf-9 cells with Autographa californica nuclear polyhedrosis virus (AcNPV) genomic DNA according to the methods of Summers et al., *A Manual of Methods for Baculovirus Vectors and Insect Cell Culture Procedures*, 1987, Texas A&M University, College Station, Tex., which is hereby incorporated by reference. Recombinant baculoviruses were recovered by visual examination and selection of occlusion-negative (occ-) plaques, and were subjected to two further rounds of plaque-purification according to the methods of Summers et al., *A Manual of Methods for Baculovirus Vectors and Insect Cell Culture Procedures*, 1987, Texas A&M University, College Station, Tex., which is hereby incorporated by reference. Protein expression from isolated virus stocks was determined by Western blot.

2. SDS-PAGE And Western Blot Detection Of Recombinant L1 Expression In Sf-9 Cells.

Infected Sf-9 cell cultures were grown in 150 cm² tissue culture flasks and prepared for analytical SDS-PAGE and Western Blot assay. Non-recombinant or recombinant L1-infected cells were collected from flasks by resuspending with a pasteur pipet, and equal numbers of wild-type or recombinant L1-infected cells were centrifuged at 500×g for 10 minutes at 4° C. Supernatants were removed and cell pellets were transferred to ice, immediately resuspended in 1 ml lysis buffer (30 mM Tris, pH 7.6; 10 mM MgCl$_2$; 1 mM CaCl$_2$; 1 MM phenylmethylsulfonyl fluoride (PMSF); leupeptin (10 µg/ml); 1% NP-40) and allowed to stand at room temperature for 15 minutes with periodic vortexing. After centrifugation at 500×g for 2 minutes at 4° C., the NP40-soluble fraction contained in the supernatant was removed and diluted 1:1 with 2× Laemmli sample buffer as described by Laemmli, "Cleavage of structural proteins during the assembly of the head of the bacteriophage T4," *Nature* 277:680–685 (1970), which is hereby incorporated by reference, and heated to 95° C. for 3 minutes. The NP40-insoluble pellet (containing nuclear material) was washed once with cold PBS (1 mM PMSF: 10 µg/ml leupeptin) and solubilized by boiling and vortexing in 1× Laemmli buffer. Samples were electrophoresed in 10% SDS polyacrylamide gels, followed by Coomassie-blue staining (FIG. 1, panel A) or blotting (FIG. 1, panel B) to an Immobilon-P membrane (Millipore Corp., New Bedford, Mass.) as described by Rose et al., "Expression of the full-length products of the HPV-6b and HPV-11 L2 open reading frames by recombinant baculovirus, and antigenic comparisons with HPV-11 whole virus particles," *J. Gen. Virol.* 71:2725–2729 (1990), which is hereby incorporated by reference.

3. Preparation Of Non-Recombinant And Recombinant L1 Stock Solutions.

These assays were performed using dilutions of clarified (high-speed) supernatant stock solutions prepared from extracts of either AcNPV or Ac11L1-infected insect cells. Suspension cultures (100 ml) of Sf-9 cells infected either with AcNPV or Ac11L1 at an approximate multiplicity of infection of 10 plaque forming units per cell were incubated at 27° C. for 72 hours. Cultures were then centrifuged at 1,000×g for 10 minutes at 4° C. and cell pellets were resuspended in 20 ml homogenization buffer (lysis buffer with 1 M NaCl) and homogenized with 50 strokes in a Dounce homogenizer on ice. Homogenates were transferred to cold 30 ml screw-cap Corex tubes and centrifuged at 3,000×g for 10 minutes at 4° C. Low-speed supernatant fractions were then transferred to a clean tube and centrifuged at 100,000×g for 30 minutes at 4° C. Total protein concentrations of high speed supernatant fractions were measured by spectrophotometric absorption at 280 nm according to the procedure of Stoscheck, "Quantitation of proteins," 1990, in *Methods in Enzymology*, vol. 182, p.54, Academic Press, Inc., New York, which is hereby incorporated by reference, and adjusted to equivalence with fresh homogenization buffer (protein concentrations approximately equal to 30 mg/ml). Glycerol was added to 10% (v/v) and stock solutions were aliquoted and stored at −20° C.

4. Western Blot And Immunodotblot Assays.

Figure 4:
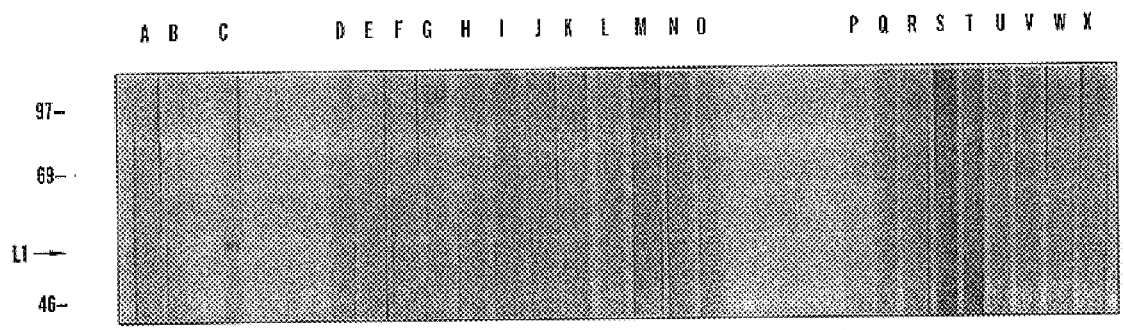
FIG. 4 shows a Western blot assay using recombinant L1 insect cell lysates. Strips A–X correspond to different primary antibodies used (strips A and B were reacted with pre- and post-immune rabbit anti-whole virus particle antisera, respectively; strip C was reacted with post-immune rabbit anti-denatured L1 common epitope antiserum; strips D–O were reacted with condyloma acuminatum patients' sera; strips P–X were reacted with control sera).

Western blot and immunodotblot assays were used to determine linear and conformational epitope antibody specificities in rabbit antisera and human sera. The Western blot assays (FIG. 3, panel A, and FIG. 4) were performed using 2 µl (about 60 µg total protein) of recombinant L1 stock solution diluted 1:100 with 1× Laemmli sample buffer, which contains protein denaturation reagents as described by Laemmli, "Cleavage of structural proteins during the assembly of the head of the bacteriophage T4," *Nature* 277:680–685 (1990), which is hereby incorporated by reference, and heated to 95° C. for 3 minutes. The denatured sample was loaded in a single 100 mm wide sample well, electrophoresed in a 10% SDS polyacrylamide gel, and blotted to an Immobilon-P membrane. After blocking with a 2% BSA solution (Kirkegaard and Perry Labs, Inc., Gaithersburg, Md.) for 2 hours at 37° C., the membrane was sliced into 24, 4 mm wide strips, each containing about 2.5 µg total protein. Thereafter, the strips were probed with antisera (FIG. 3, panel A, and FIG. 4).

For immunodotblot analysis, non-recombinant or recombinant L1 stock solutions were diluted 1:1,000 with cold PBS (1 mM CaCl$_2$ and 100 µl aliquots (containing about 3.0 µg total protein) were dotted onto an Immobilon-P membrane. Protein denaturation reagents were omitted from the immunodotblot sample preparation to preserve the native conformation of recombinant L1. Blocking, primary and secondary antibody diluent solutions, washes, and substrate used are as described by Strike et al., "Expression in *Escherichia coli* of seven DNA segments comprising the complete L1 and L2 open reading frames of human papillomavirus type 6b and the location of the (common antigen)," *J. Gen. Virol.* 70:543–555 (1989), which is hereby incorporated by reference. Primary antibody incubations were performed overnight at 4° C., second antibody incubations were done at room temperature for 90 minutes. For immunodotblots, all solutions except the substrate solution contained $CaCl_2$ at 1 mM. Primary antibody dilutions were 1:2,000 for rabbit antisera and 1:1,000 for human sera. Specifically-bound antibodies were detected with affinity-purified anti-rabbit (Kirkegaard and Perry Laboratories, Inc., Gaithersburg, Md.), or anti-human (TAGO Immunodiagnostics, Burlingame, Calif.) IgG-alkaline phosphatase conjugates used at dilutions of 1:2,000 and 1:5,000, respectively, using BCIP/NBT (Kirkegaard and Perry Laboratories, Inc.) as substrate. Immunodotblot reactions were assessed by visual comparison of non-recombinant and recombinant L1 dot intensities. A reaction was considered positive if the color intensity of the recombinant L1 dot was greater than the color intensity of the non-recombinant control dot present on the same strip.

5. Antisera.

The denatured L1 antiserum used was described previously as anti-pEX480 by Strike et al., "Expression in *Escherichia coli* of seven DNA segments comprising the complete L1 and L2 open reading frames of human papillomavirus type 6b and the location of the (common antigen)," *J. Gen. Virol.* 70:543–555 (1989), which is hereby incorporated by reference. This antiserum was obtained by rabbit immunization with a gel-purified bacterially-expressed fusion protein that contained a 160 amino acid sequence derived from the mid-region of the HPV-6b L1 open reading frame fused to the carboxy terminus of betagalactosidase, as described by Stanley et al., "Construction of a new family of high efficiency bacterial expression vectors: Identification of cDNA clones coding for human liver proteins," *EMBO. J.* 3:1429–1434 (1984); and Strike et al., "Expression in *Escherichia coli* of seven DNA segments comprising the complete L1 and L2 open reading frames of human papillomavirus type 6b and the location of the (common antigen)," *J. Gen. Virol.* 70:543–555 (1989), which are hereby incorporated by reference. This sequence contains the papillomavirus L1 common antigen as described by Strike et al., "Expression in *Escherichia coli* of seven DNA segments comprising the complete L1 and L2 open reading frames of human papillomavirus type 6b and the location of the (common antigen)," *J. Gen. Virol.*, 70:543–555 (1989), which is hereby incorporated by reference. The rabbit whole virus particle antiserum used was as described by Bonnez et al., "Antibody-mediated neutralization of human papillomavirus type 11 (HPV-11) infection in the nude mouse: Detection of HPV-11 mRNAs by the polymerase chain reaction," *J. Inf. Dis.*, 165:376–380 (1992), which is hereby incorporated by reference, and produced by immunization of rabbits with purified non-denatured HPV-11 virions, which were obtained from athymic mouse foreskin xenografts according to Bonnez et al., "Antibody-mediated neutralization of human papillomavirus type 11 (HPV-11) infection in the nude mouse: Detection of HPV-11 mRNAs by the polymerase chain reaction," *J. Inf. Dis.*, 165:376–380 (1992); and Kreider et al., "Laboratory production in vivo of infectious human papillomavirus type 11," *J. Virol.*, 61:590–593 (1989), which are hereby incorporated by reference. Patients' sera were obtained from individuals with biopsy-proven condyloma acuminatum. Serum specimens previously found positive by HPV-11 whole virus particle-based ELISA as described by Bonnez et al., "Use of human papillomavirus type 11 virions in an ELISA to detect specific antibodies in humans with condylomata acuminata," *J. Gen. Virol.*, 72:1343–1347 (1991), which is hereby incorporated by reference, were used to maximize the ability to detect antibodies directed against VLPs. Control sera were obtained from nuns who professed no lifetime sexual contact. These sera were negative for HPV-11 antibodies as determined by the HPV-11 particle-based ELISA as described by Bonnez et al., "Use of human papillomavirus type 11 virions in an ELISA to detect specific antibodies in humans with condylomata acuminata," *J. Gen. Virol.*, 72:1343–1347 (1991), which is hereby incorporated by reference.

6. Production and Purification of HPV-11 L1 Virus-like Particles.

Figure 2:
FIG. 2 shows an electron micrograph of HPV-11 virus-like particles recovered by sucrose density centrifugation from Ac11L1-Infected SF-9 cells. The VLPs shown are approximately 52 nm in diameter (scaled by magnification standards) and possess icosahedral symmetry, consistent with published observations regarding the morphologic characteristics of naturally-occurring papillomavirions.
Figure 6:
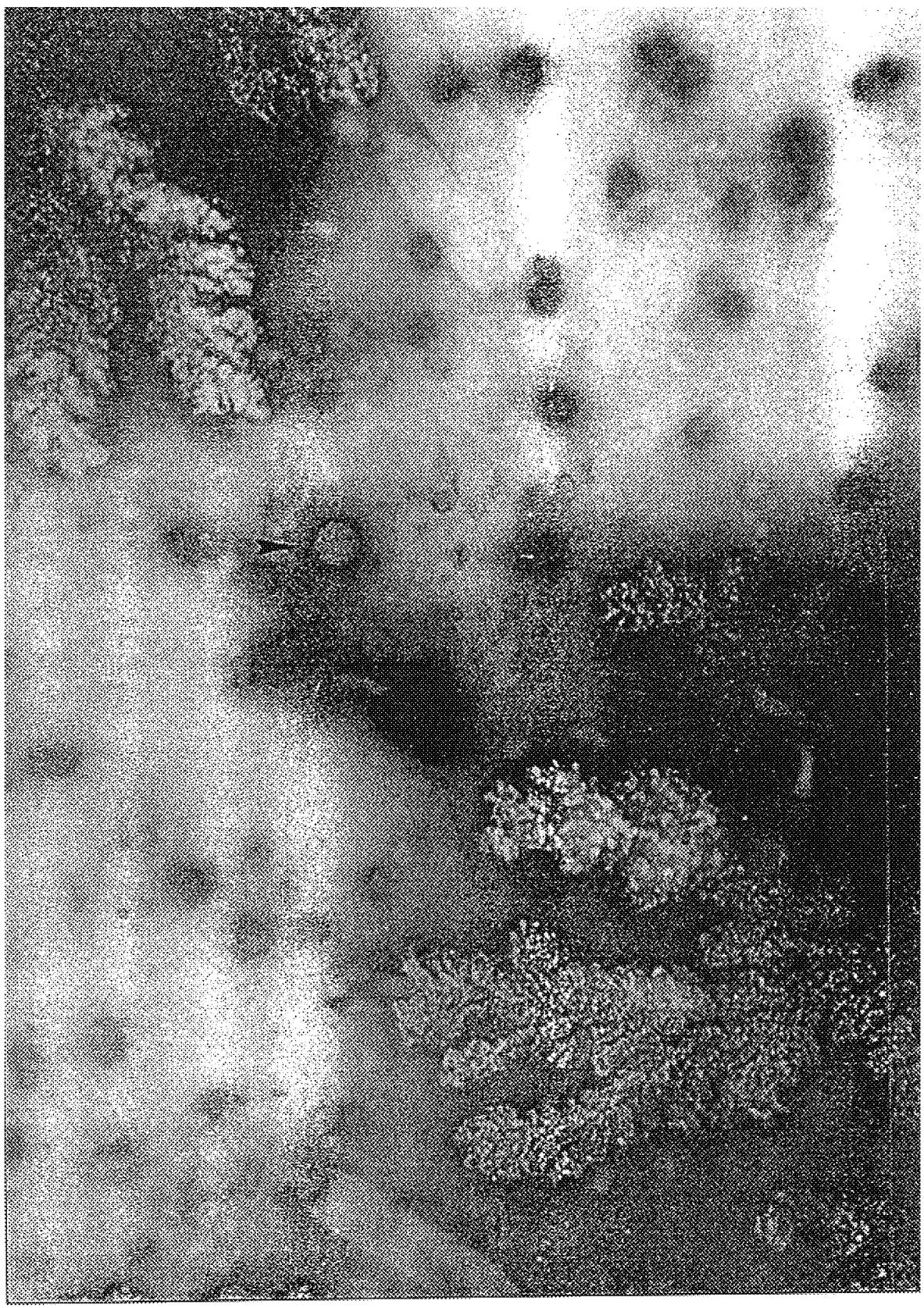
FIG. 6 is an electron micrograph of HPV type 6 VLPs, produced by the construction and expression of an HPV-6 L1 recombinant baculovirus (Ac6L1).
Figure 7:
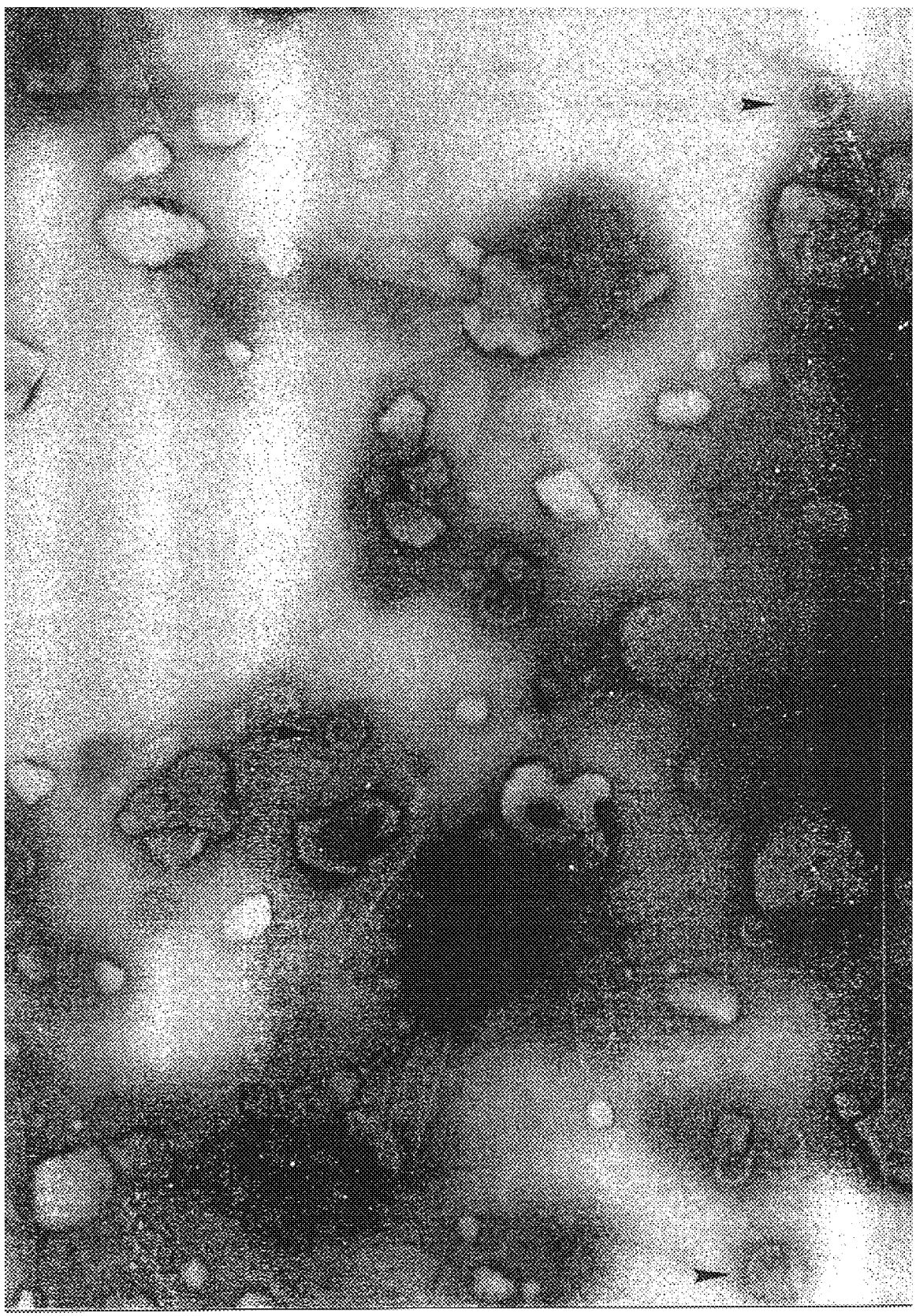
FIG. 7 is an electron micrograph of HPV type 16 VLPs, produced by the construction and expression of an HPV-16 L1 recombinant baculovirus (Ac16L1).

Recombinant VLPs were purified directly from the cell-free culture supernatant of Ac11L1-infected Sf-9 cell suspension cultures by a series of low and high speed centrifugation steps. Infected Sf-9 cells were pelleted from a 200 ml suspension culture a low speed (1,000×g) and the cell-free supernatant was centrifuged again at high speed (100,000× g) for 90 minutes at 4° C. The high-speed pellet was resuspended in buffer A (50 mM Tris, pH 8.0; 1 M NaCl; 10 mM $MgCl_2$; 10 mM $CaCl_2$; 2 mM phenylmethylsulfonyl fluoride (PMSF); 10 µg/ml Leupeptin), 5.2 g solid CsCl were added, and the final volume was adjusted to a total of 13 ml with fresh buffer A (0.4 g/ml final concentration). After centrifugation (100,000×g, 22 hours, 10° C.), the single band obtained was removed and diluted with 12 ml of fresh buffer A (without CsCl) and centrifuged again (100,000×g, 90 minutes, 4° C.) to pellet purified VLPs. VLPs purified by sucrose density gradient centrifugation were identified by electron microscopy after staining with 2% neutral buffered phosphotungstic acid (FIGS. 2, 6, and 7).

EXAMPLE II

Figure 1B:
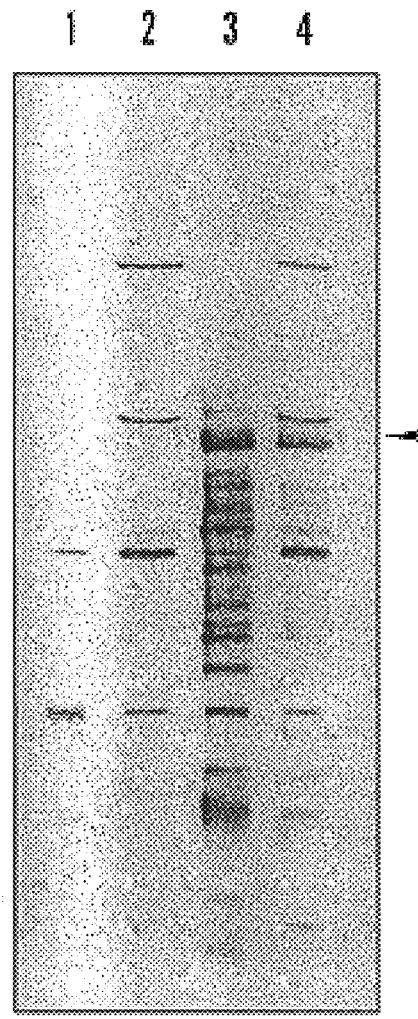
FIG. 1B shows a Western blot of wild-type AcNPV and recombinant Ac11L1-infected SF-9 cell lysates probed with rabbit polyclonal antiserum specific for HPVL1 common epitope.

Expression And Immunologic Detection Of Recombinant HPV-11 L1 Protein In Sf-9 cells SDS-PAGE analysis of total Sf-9 cell proteins from insect cells infected with the recombinant virus Ac11L1 demonstrated a novel 55 kD protein seen by Coomassie-blue staining in Ac11L1-infected cells (FIG. 1A, lane 3). With reference to FIGS. 1 (A and B), FIG. 1A shows Coomassie-stained SDS polyacrylamide gel of wild-type AcNPV and recombinant Ac11L1-infected Sf-9 cell lysates and FIG. 1B shows Western blot of wild-type AcNPV and recombinant Ac11L1-infected Sf-9 cell lysates probed with a rabbit polyclonal antiserum specific for the HPV L1 common epitope. Non-recombinant (lanes 1,2) and recombinant L1-infected (lanes 3,4) Sf-9 cell lysates were fractionated into insoluble (lanes 1,3) and soluble (lanes 2,4) fractions, and electrophoresed on 10% polyacrylamide gels. Molecular reference ($M_r$) markers are displayed at the left, and the arrow at the right indicates the approximate position of recombinant L1 (about 55 kD $M_r$). This protein is not present in wild-type AcNPV lysates, and co-migrates with a protein that is immunoreactive (FIG. 1B, lanes 3 and 4) with a rabbit antiserum prepared against the linear HPV L1 common antigen as described by Strike et al., "Expression in *Escherichia coli* of seven DNA segments comprising the complete L1 and L2 open reading frames of human papillomavirus type 6b and the location of the (common antigen)," *J. Gen. Virol.* 70:543–555 (1989), which is hereby incorporated by reference. Lower $M_r$ L1-immunoreactive bands were also detected and may be derived from degradation of the full-length L1 product (FIG. 1B, lanes 3 and 4).

Although the predominant portion of L1 produced in this system appeared in the NP40-insoluble fraction, approximately 25–30% was present in the NP40-soluble fraction (FIG. 1B, lane 4). Maximal L1 accumulation occurred at 72 hours post-infection.

EXAMPLE III

Electron microscopic visualization of VLPs

Figure 12A:
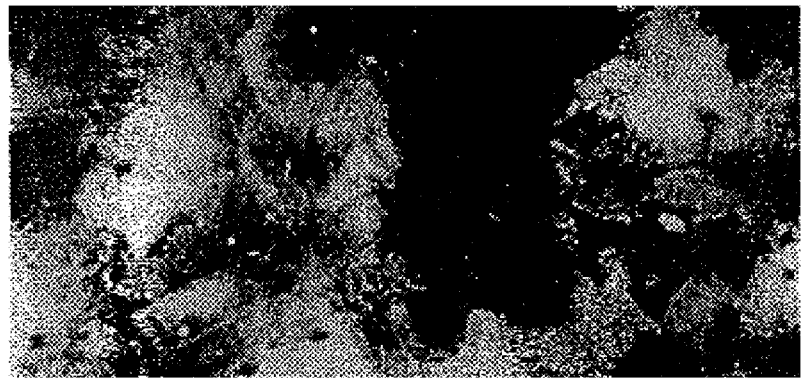
FIG. 12 shows an electron microscopic analyses of crude and CsCl-purified VLP preparations (A-VLPs pelleted from Ac11L1-infected Sf-9 cell-free culture supernatant; B-CsCl-purified VLPS; bar=50 nm)
Figure 12B:
Figure 16A:
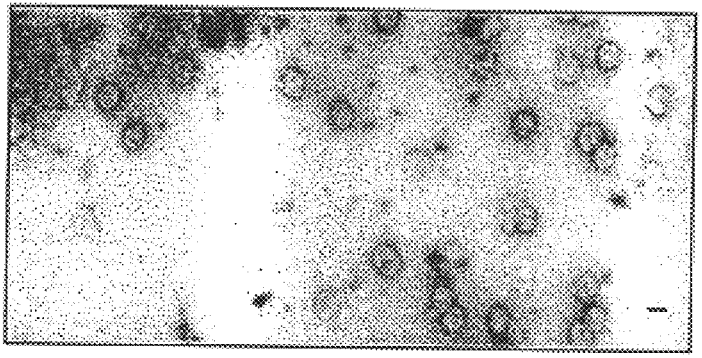
FIG. 16(A–C) shows an electron micrograph of cesium chloride-purified VLPs derived from HPV types 11, 16 and 18. VLPs were purified as described in the specification and negatively-stained with 2% phosphotungstic acid. A) HPV-11 L1 VLPs; B) HPV-16 L1 VLPs; C) HPV-18 L1 VLPs; Bars correspond to 100 nm.
Figure 16B:
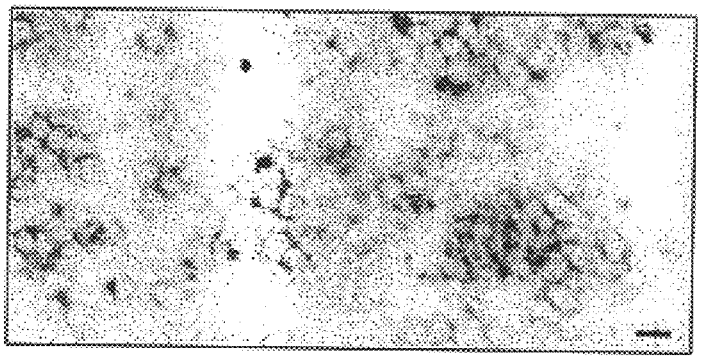
Figure 16C:
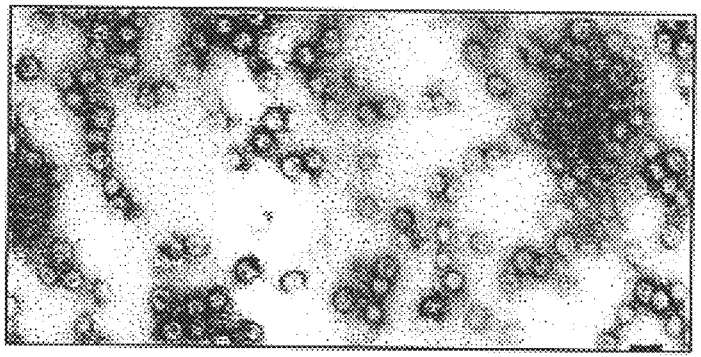

Electron micrographs of negatively stained preparations of sucrose banded VLPs (FIGS. 2, 6, and 7) showed distinct VLPs. FIG. 2 shows HPV-11 capsid-like particles which were present at the 50–60% interface of the sucrose density gradient. FIG. 6 shows HPV type 6b (HPV-6b) capsid-like particles which resulted from the expression of the HPV-6b L1 coding sequence in the baculovirus system, and which were purified in exactly the same manner. FIG. 7 demonstrates that this method is also suitable for the production of HPV type 16 (HPV-16) VLPs, upon expression of the HPV-16 L1 coding sequence. FIGS. 12 & 16 demonstrate that VLPs can be purified by cesium chloride density gradient centrifugation as well. Particle diameters determined by direct measurement of the VLPs in FIG. 2, were approximately 52 nm. This measurement is consistent with the diameter of isolated papillomavirus virions as described by Klug et al., "Structure of viruses of the papilloma-polyoma type I: Human wart virus," *J. Mol. Biol.* 11:403–423 (1965), which is hereby incorporated by reference.

EXAMPLE IV

Immunoreactivity Of HPV-11 VLP-Containing Insect Cell Extracts With Rabbit Antisera The immunologic properties of the recombinant L1 protein were studied using rabbit antisera that reacted with native or denatured L1 protein epitopes. Rabbit antiserum pEX480, directed against the common papillomavirus antigen, reacted well with denatured recombinant L1 in Western blot assays, but did not react with the same antigen preparation by immunodotblot, a type of immunoassay in which the antigen is placed on the blotting membrane under non-denaturing conditions (FIG. 3, compare strips A). In contrast to the pattern of reactivity exhibited by anti-pEX480, the rabbit polyclonal antiserum raised against HPV-11 whole virus particles did not react with recombinant L1 by Western blot, but reacted strongly with recombinant L1 in the immunodotblot assay (FIG. 3, compare strips C). This reactivity was specific as demonstrated by lack of reactivity in the post-immune serum against the native non-recombinant control preparation (FIG. 3, panel B, strip C). Rabbit antiserum pEX215 was included in these immunoassays to allow comparison of the relative amounts of L1 present in the two types of immunoassays. The level of immunoreactivity of the pEX215 antiserum with recombinant L1 in both formats is roughly equivalent (FIG. 3, strips B), indicating that the amounts of L1 present are approximately equal. Furthermore, the observation that this antiserum is able to react with L1 in both formats suggests that the linear immunoreactive L1 amino-terminal epitope(s) recognized by the pEX215 antiserum is not obscured by the adoption of higher-order L1 conformation.

EXAMPLE V

Immunoreactivity Of VLP-Containing Insect Cell Extracts With Human Sera

Figure 5:
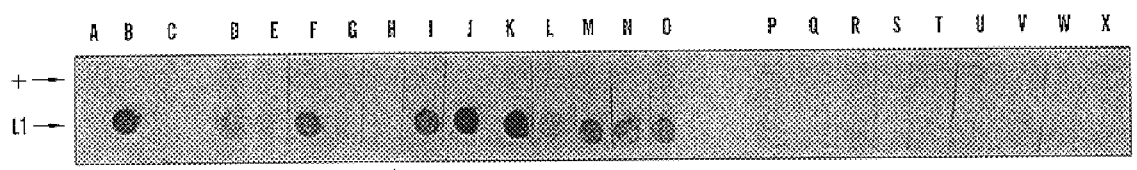
FIG. 5 shows an immunodotblot assay using insect cell lysates. The letters above the strips correspond to different primary antibodies used, which were the same as described in FIG. 4.

To determine the prevalence of antibodies in human sera directed against linear versus conformational epitopes, sera obtained from individuals with biopsy-proven condyloma acuminatum were evaluated in Western blot and immunodotblot assays using VLPs as antigen. None of the patients' or control sera were immunoreactive with denatured recombinant L1 by Western blot (FIG. 4, strips D–O (patients) and P–X (controls)). Conversely, 11 of 12 patients' sera (FIG. 5, strips D–O were read as positive, with the exception of strip H) and 0 of 9 control sera (FIG. 5, strips P–X) were immunoreactive with recombinant L1 by immunodotblot, a highly statistically significant difference ($p=7\times10^{-5}$; Fisher's exact test). This result correlates well with results previously obtained using the same sera in an HPV-11 particle-based ELISA as described by Bonnez et al., "Use of human papillomavirus type 11 virions in an ELISA to detect specific antibodies in humans with condylomata acuminata," *J. Gen. Virol.* 72:1343–1347 (1991), which is hereby incorporated by reference.

EXAMPLE VI

ELISA Assay

CsCl-purified VLPs were quantitated by spectrophotometer ($A_{280}$) and diluted to a concentration of 8 ng/ul in cold PBS. Aliquots (100 μl) of either PBS or diluted VLP solution (800 ng total protein) were loaded into wells and plates were allowed to stand at 4° C. overnight. Plates were blocked for 2 hours at room temperature with a 1% BSA solution, followed by the addition of antisera, in duplicate, at a dilution of 1:100. Primary antisera were reacted at room temperature for 90 minutes. Plates were washed four times and secondary antibody (goat anti-Human IgG-alkaline phosphatase conjugate) was added (TAGO, 1:5000) and plates were allowed to stand at room temperature for 90 minutes. Substrate was added to each well and absorbance at 405 nm was read. Specific absorbance was calculated by subtracting the PBS absorbance from the VLP absorbance for each replicate, and taking the average absorbance value.

The result obtained using VLPs (FIG. 8) were equivalent to results previously reported in an ELISA test of the same sera (from RRP patients), which used HPV-11 whole virus particles as antigen (50%). Good correlation with results from a previous whole virus particle-based ELISA is given in FIG. 9 ($r^2=0.75$).

EXAMPLE VII

Western Blot and Immunodotblot

Sf-9 suspension cultures (100 ml) were infected with either AcNPV (non-recombinant control), Ac11L1, or Ac16L1 recombinant baculoviruses as previously described by Rose et al., *J. Virol.*, 67:1936–1944 (1993), which is hereby incorporated by reference, and incubated 72 hours at 27° C. With reference to FIG. 11, samples were prepared, electrophoresed, and immunoblotted as previously described by Rose et al., *J. Virol.*, 67:1936–1944 (1993); and Rose et al., *J. Gen. Virol.*, 71:2725–2729 (1990), which are hereby incorporated by reference. VLPs were present in both sample preparations, as verified by electron microscopy (data not shown). Total sample protein concentrations were equilibrated prior to use by spectrophotometer ($A_{280}$).

Figure 10:
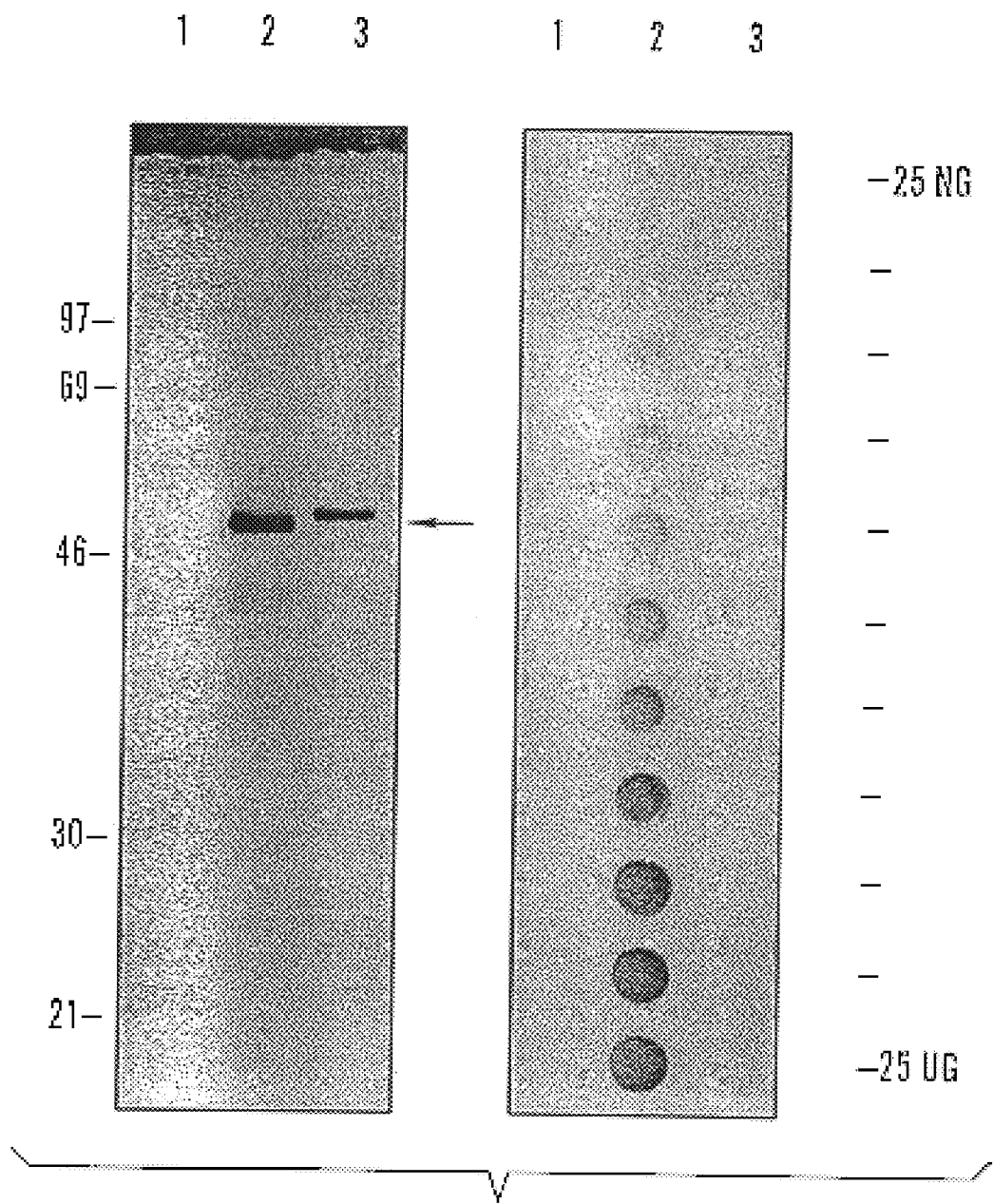
FIG. 10(a) shows a Western blot (left panel) of HPV-11 L1 (Lane 2) and HPV-16 L1 (Lane 3) proteins. Molecular reference markers are at the left, the arrow indicates the approximate positions of the HPV-11 and HPV-16 recombinant L1 proteins.
FIG. 10(b) is an Immunodotblot (right panel) where Lane 1: AcNPV (wild-type baculovirus-infected sample); Lane 2: Ac11L1 (recombinant Ac11L1-infected sample); Lane 3: Ac16L1 (recombinant Ac16L1-infected sample).

With reference to FIG. 10(a), samples (20 μg total protein/lane) were electrophoresed in a 10% SDS-polyacrylamide gel and Western blotted overnight as previously described by Bonnez et al., *J. Inf. Dis.* 165:376–380 (1992), which is hereby incorporated by reference. The nitrocellulose blot was probed with rabbit antiserum R5-409, used at a dilution of 1:1000 as described by Christensen et al., *Virus Research* 21:169–179 (1991), which is hereby incorporated by reference. As shown in FIG. 10(*a*) (left panel), recombinant HPV-11 L1 (lane 2) and recombinant HPV-16 L1 (lane 3) proteins were detected in approximately equal amounts by anti-papillomavirus L1 common epitope antiserum R5-409. The predicted amino acid sequence of the HPV-16 L1 protein is five amino acids longer than the predicted sequence of the HPV-11 L1 protein, which is consistent with the slightly slower rate of migration exhibited by the recombinant HPV-16 L1 protein.

With reference to FIG. 10(*b*), samples were diluted (two-fold serial dilutions made with PBS) and applied to nitrocellulose under non-denaturing conditions, beginning with a total protein concentration of 25 $\mu$g (bottom), and ending with a total protein concentration of 25 ng (top)). Rabbit antiserum R-366 was used at a dilution of 1:1000. In the right panel (i.e., the immunodotblot), the whole virus particle antiserum detected the native recombinant HPV-11 L1 VLP preparation over a 1000-fold dilution range. However, this same hyperimmune rabbit antiserum was not immunoreactive with the native recombinant HPV-16 L1 VLP preparation, even at a higher concentration of antigen (25 $\mu$g) than that used for analysis by Western blot (20 $\mu$g).

The hyperimmune rabbit native HPV-11 virion neutralizing antiserum did not cross-react with native HPV-16 L1 protein, suggesting that the conformational epitope(s) of the HPV-11 capsid that is recognized by this antiserum is immunologically distinct from conformational epitopes present in the HPV-16 VLP preparation.

EXAMPLE VIII

Western Immunoblot Assay

VLPs were detected in, and purified directly from, the supernatant medium of an Ac11L1-infected Sf-9 cell suspension culture (200 ml). Cells were pelleted at low speed (1000×g) and the cell-free supernatant was then centrifuged at high speed (100,000×g). Cells were removed by low speed centrifugation (1000×g), and VLPs were prepared from culture supernatants as previously described in Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference. FIG. 11A is a 10% SDS-polyacrylamide gel stained with coomassie blue. FIG. 11B is a western immunoblot of an identically loaded gel, probed with a rabbit antiserum specific for the HPV common antigen as described by Strike et al., *J. Gen. Virol* 70:543–555 (1989), which is hereby incorporated by reference, used at a dilution of 1:1000. Examination of the high-speed pellets obtained from non-recombinant or recombinant L1-infected Sf-9 cell culture supernatants indicated the presence of VLPs in the recombinant L1-infected supernatant fraction. The resuspended recombinant L1 high-speed pellet was purified by equilibrium density gradient centrifugation as previously described in Bonnez et al., *J. Inf. Dis.* 165:376–380 (1992), which is hereby incorporated by reference. The single band obtained by this method was removed with a sterile 18 gauge needle, diluted with fresh buffer A (50 mM Tris, pH 8.0; 1 M NaCl; 10 mM MgCl$_2$; 10 m M CaCl$_2$; 2 mM phenylmethylsulfonyl fluoride (PMSF); 10 $\mu$g/ml Leupeptin) to a volume of 12 ml, and again centrifuged at 100,000×g for 90 minutes at 4° C. After resuspension of the pellet in 0.5 ml of fresh buffer A (50% glycerol), electron microscopic analysis of a portion of the sample, negatively stained with 2% phosphotungstic acid, confirmed the presence of intact HPV VLPs (FIG. 12).

Figure 13A:
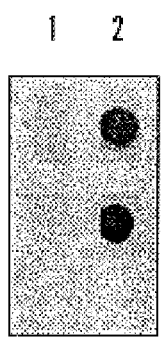
FIG. 13 shows immunodotblot analyses of purified recombinant VLPs and HPV-11 whole virions (Lane 1: Pre-immune sera; lane 2: post-immune sera; A-Rabbit R-366, immunized with purified HPV-11 whole virions; B-Rabbit R-399, immunized with purified HPV-11 VLPs; Antigens: VLP (HPV-11 L1 virus-like particles); WVP (HPV-11 whole virus particles)).
Figure 13B:

As previously described, recombinant VLPs were immunoreactive with antibodies directed against HPV-11 whole virus particles. (See Rose et al., *J. Virol.* 67:1936–1944 (1993), which is hereby incorporated by reference.) In this study, applicants immunized rabbits with purified VLPs and tested the post-immune sera for immunoreactivity with whole virions. New Zealand white rabbits were immunized intramuscularly at two sites with a 1:1 emulsion of purified VLPs (~20 $\mu$g protein) in complete Freund's adjuvant (0.25 ml per site). Boosts were given after 30 days with a VLP emulsion prepared in incomplete Freund's adjuvant, and immune sera were collected 14 days later. Sera were reacted with either native HPV-11 virions or recombinant VLPs in a dotblot immunoassay, as previously described in Rose et al., *J. Virol.* 67:1936–1944 (1993), which is hereby incorporated by reference. The immunologic cross-reactivity of anti-VLP antibodies with whole virions, as shown in FIG. 13, demonstrates that VLPs are immunogenic, and appear to faithfully replicate the antigenic profile of infectious HPV-11 virions. With reference to FIG. 13, non-denatured purified sample preparations were applied to nitrocellulose as described by Rose et al., *J. Virol.* 67:1936–1944 (1993), which is hereby incorporated by reference.

EXAMPLE IX

Neutralization Activity

Figure 14:
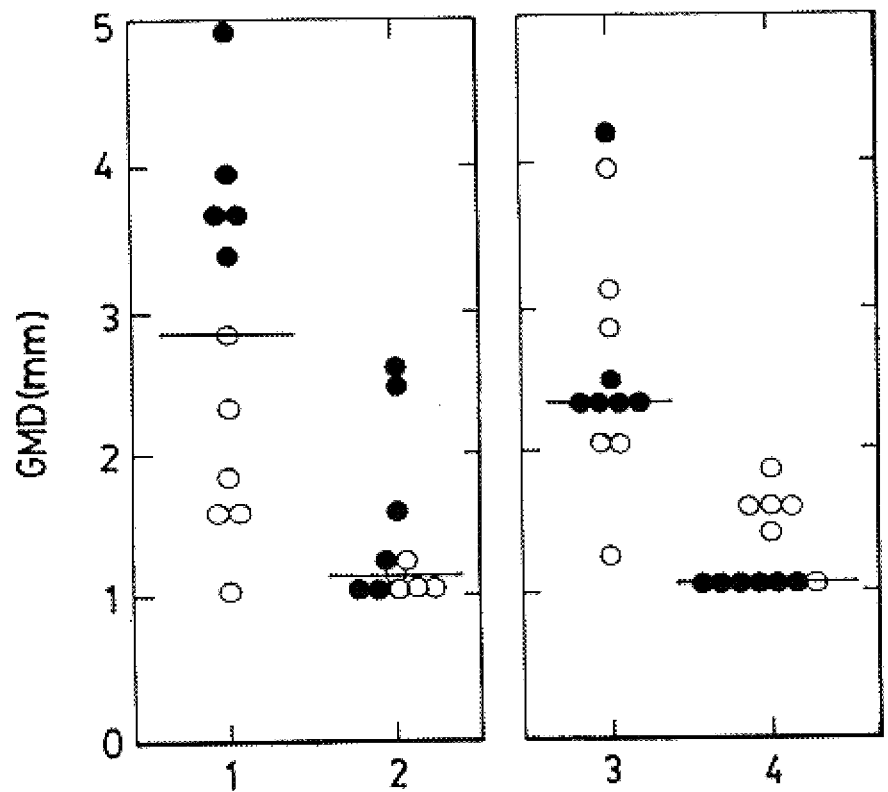
FIG. 14 shows a dotplot analysis of xenograft geometric mean diameters (GMD).

The preparation of the infection HPV-11 $_{Hershey}$ viral suspension (originally provided by John Kreider, Department of Pathology and Microbiology and Immunology, The Milton S. Hershey Medical Center, Hershey, Pa.) has been described by Bonnez et al., *J. Inf. Dis.* 165:376–380 (1992), which is hereby incorporated by reference. In four parallel experiments, 450 $\mu$l of the infecting viral suspension (batch 4/90) were incubated at 37° C. for 1 hour with 50 $\mu$l (1:10 final dilution) of either preimmune anti-HPV-11 serum (group 1), post-immune anti-HPV-11 serum (group 2), pre-immune anti-VLP serum (group 3), or post-immune anti-VLP serum (group 4). Groups 1 and 2 were neutralization controls that have described previously by Bonnez et al., *J. Inf. Dis.* 165:376–380 (1992), which is hereby incorporated by reference., and groups 3 and 4 were the test groups. The preparation of human foreskins excised for routine circumcision has also been described by Bonnez et al., *J. Gen. Virol.* 72:1343–1347 (1991), which is hereby incorporated by reference. Foreskins were cut into 1×1 mm squares and small number of fragments from each foreskin used were snap frozen and saved. The remaining fragments were divided equally into four groups, and each group was added to one of the four viral suspension-serum mixtures at the end of the incubation period. Mixtures were incubated for 1 hour at 37° C. For each experimental group, one foreskin fragment was placed under the renal capsule of each kidney of 3 female, litter-matched, 4–6 week old athymic nu/nu mice on a BALB/c background (Taconic Farms, Germantown, N.Y.). The experiment was replicated on a different day, with a different foreskin. Thus, for each experimental group a total of 12 grafts were implanted. The animals were sacrificed 12 weeks after grafting, at which time the grafts were removed and processed. (See Bonnez et al., *J. Inf. Dis.* 165:376–380 (1992), which is hereby incorporated by reference). With reference to FIG. 14, grafts were prepared for analysis as described herein and infected with viral lysate that was pre-treated with either (1) pre-, and (2) post-immune rabbit HPV-11 whole virus particle sera, or (3) pre-, and (4) post-immune rabbit HPV-11L1 virus-like particle sera. The filled circles correspond to the first replicate experiment, the open circles to the second replicate experiment. The horizontal bars indicate the median GMD. For graft size comparison, the geometric mean diameter (GMD) was calculated by taking the cubic root of the product of the length, width, and height of the recovered grafts.

At the time of euthanasia, one graft was missing from each of the neutralization control pre- and post-immune anti-HPV-11 treated groups. Thus, the number of grafts available for analysis in each of these groups was 11 (FIG. 14). The median [range] GMDs (mm) of the grafts in the pre- and post-immune control groups were respectively 2.9 [1.0, 4.9] and 1.3 [1.0, 2.6]. The difference, 1.6 mm, was statistically significant (P=0.004, Mann-Whitney U test). All 12 implanted grafts were available for analysis in both the pre- and post-immune anti-VLP antibody-treated groups (FIG. 4). The median [range] GMDs (in mm) of the grafts were respectively 2.3 [1.3, 4.2] and 1.0 [1.0, 1.8]. The difference in size, 1.3 mm, was statistically significant ($p<10^{-4}$). Although the difference in graft sizes between the first and second experiment was not statistically significant (P=0.62) in the preimmune group, it was significant (P=0.007) in the post-immune group. Therefore, applicants compared the differences in graft sizes between the pre- and post-immune anti-VLP antibody-treated groups within each replicate experiment. Both were statistically significant (P=0.002 and P=0.04, respectively for the first and second replicate). cl EXAMPLE X Source of Viral DNAs The source of HPV-11 genomic DNA (Bonnez et al., *J. Gen. Virol.* 72:343–1347 (1991), which is hereby incorporated by reference) and construction of the Ac11L1 recombinant baculovirus (Rose et al., *J. Virol.*, 67:1936–1944 (1993), which is hereby incorporated by reference) have been described. The HPV-16 genomic DNA was recovered from a CIN III lesion and standard cloning methods were used to construct the Ac16L1 baculovirus (Chesters and McCance, unpublished data). The HPV-18 L1 sequence was amplified by polymerase chain reaction from the HPV-18 prototype (provided by H. zur Hausen) and used to construct the Ac 18L1 baculovirus by the same procedure used for the construction of Ac11L1 (Rose et al., *J. Virol.*, 67:1936–1944 (1993), which is hereby incorporated by reference).

EXAMPLE XI

Purification of Recombinant VLPs

Figure 15:
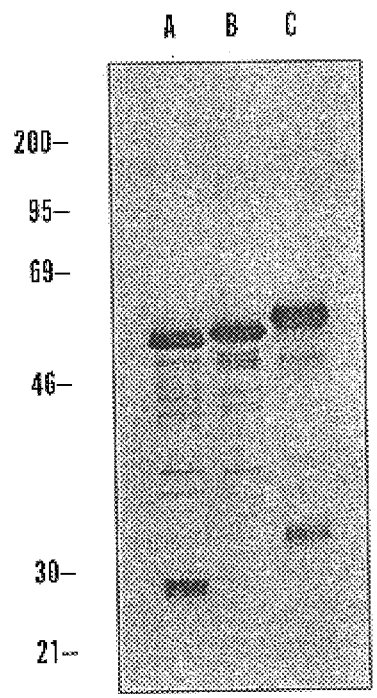
FIG. 15 shows a Western blot immunoassay of HPV-11, HPV-16 and HPV-18 purified VLP preparations (Lane A, HPV-11 L1 VLPs; lane B, HPV-16 L1 VLPs; lane C, HPV-18 L1 VLPs).

Recombinant VLPs were purified as described by Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference. Single bands containing purified HPV-11, HPV-16, or HPV-18 VLPs were removed from CsCl density gradients by syringe, diluted with buffer A (phosphate-buffered saline (PBS); 1 mM Mgcl$_2$; 1 mM CaCl$_2$; 1 mM phenylmethylsulfonylfluoride (PMSF)) to 12 ml, and sedimented at 100,000×g for 90 minutes at 4° C. Pellets were resuspended in 200 µl of buffer A containing 50% glycerol, quantitated by spectrophotometry (280 nm), and stored at −20° C. Recombinant L1 proteins were analyzed by SDS-PAGE and Western blot immunoassay as previously described (Rose et al., *J. Virol.* 67:1936–1944 (1993), which is hereby incorporated by reference). Samples containing 5 µg of purified HPV-11, -16, or -18 VLPs were electrophoresed, blotted, and probed with anti-papillomavirus L1 (anti-PVL1) common antigen rabbit antiserum as previously described (Strike et al., *J. Gen. Virol.* 70:543–555 (1989); and Rose et al., *J. Virol.* 67:1936–1944 (1993), which are hereby incorporated by reference). Predicted coding capacities of the HPV-11, -16, and -18 L1 open reading frames (ORFs) are 501 amino acids (Dartmann et al., *Virology* 151:124–130 (1986), which is hereby incorporated by reference), 505 amino acids (Seedorf et al., *Virology* 145:181–185 (1985), which is hereby incorporated by reference), and 507 amino acids (Cole et al., *J. Mol Biol.* 193:599–608 (1987), which is hereby incorporated by reference), respectively, and an L1-immunoreactive band of the expected size (~55 kD $M_r$) appeared in each of the three sample preparations tested by Western blot immunoassay (FIG. 15). Lower molecular weight L1-immunoreactive proteins were also detected by Western blot immunoassay of the CsCl-purified VLP preparations (FIG. 15), and are likely to be degradation products of full-length L1 proteins, as relative amounts of these proteins varied in subsequent analyses (data not shown). However, the major 55 kD $M_r$L1-immunoreactive bands in each of the samples did not vary, either in their mobilities or their relative amounts (data not shown). Electron microscopy of purified samples (negatively-stained with 2% phosphotungstic acid) confirmed VLP formation in HPV-11 (FIG. 16A), HPV-16 (FIG. 16B) and HPV-18 (FIG. 16C) VLP preparations.

EXAMPLE XII

Preparation of Rabbit VLP Immune Sera and Conditions of the ELISA

Figure 17:
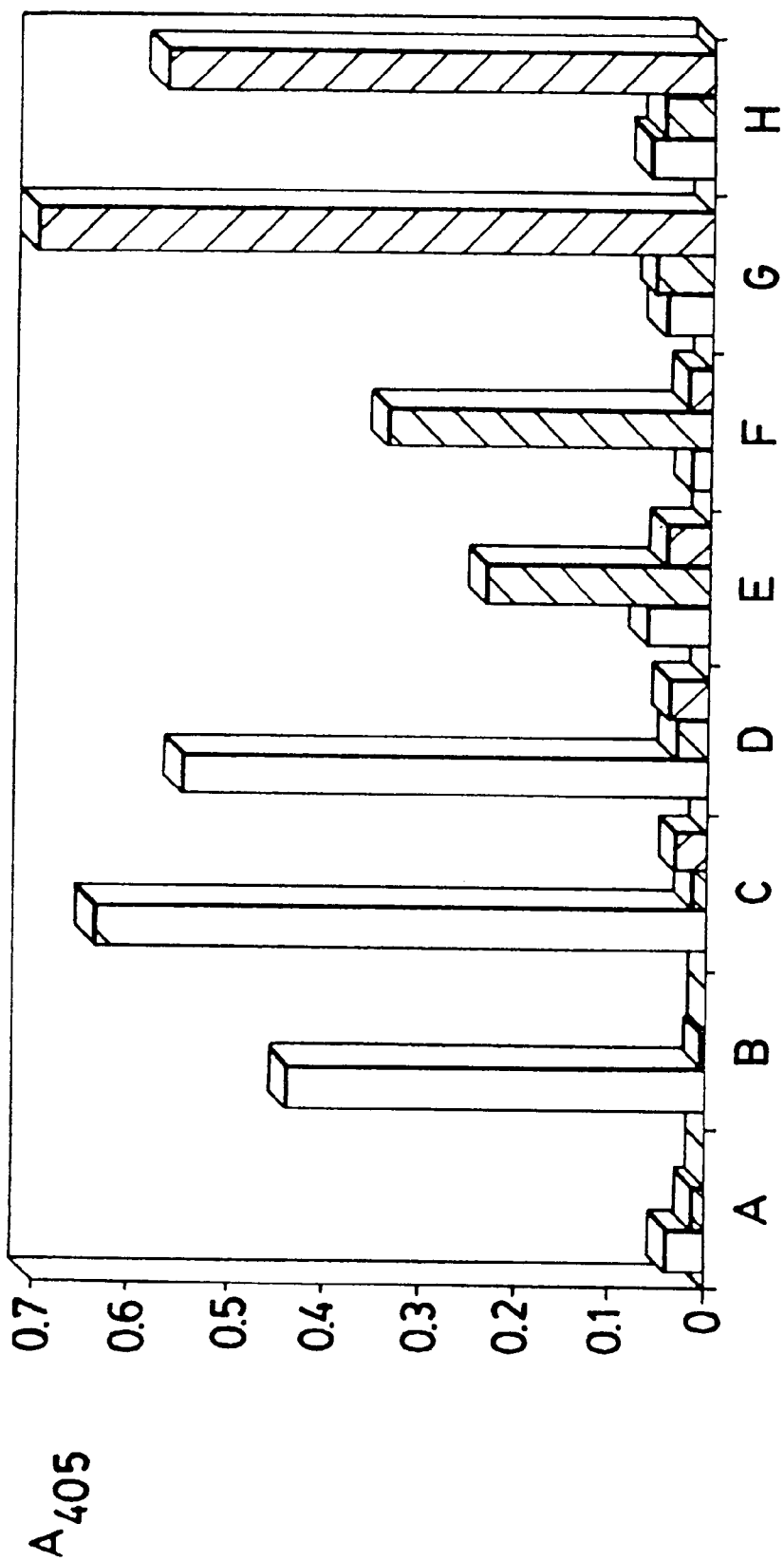
FIG. 17 shows immunoreactivities of VLP rabbit post-immune antisera with homologous and heterologous VLP preparations. Antigens: HPV-11 L1 VLPs, white bars; HPV-16 L1 VLPs, stippled bars; HPV-18 L1 VLPs, black bars. Antisera: A) Anti-PVL1 common antigen rabbit antiserum; B) HPV-11 whole virion rabbit antiserum; C,D) from two rabbits immunized with HPV-11 L1 VLPs; E,F) from two rabbits immunized with HPV-16 L1 VLPs; G,H) from two rabbits immunized with HPV-18 L1 VLPs FIG. 18 (A–B) depicts the kinetics of serum IgG and IgA antibody responses after oral immunization with HPV-11 recombinant VLPs. Pre- and post-immune sera were evaluated in an HPV-11 VLP ELISA. Orally immunized mice received either 100 μg (triangles), 50 μg (squares), or 10 μg (diamonds) of HPV-11 VLPs. A fourth group of mice received no inoculations (circles). Booster inoculations were administered in the same way at the indicated timepoints (arrows).

HPV-11, HPV-16, and HPV-18L1 VLP rabbit immune sera were prepared by immunizing two New Zealand white rabbits intramuscularly at two sites with each of the VLP preparations (i.e., six rabbits were immunized), using previously described methods (Bonnez et al., *J. Inf. Dis.* 165:376–380 (1992); Rose et al., *J. Virol.* 67:1936–1944 (1993), which are hereby incorporated by reference). Rabbit anti-PVL1 common antigen (Strike et al., *J. Gen. Virol.* 70:543–555 (1989), which is hereby incorporated by reference), HPV-11 whole virion (Bonnez et al., *J. Inf. Dis.* 165:376–380 (1992), which is hereby incorporated by reference), and HPV-11, -16, and -18 VLP antisera were tested with ELISA against the three recombinant VLP preparations (FIG. 17). For this ELISA, purified VLPs were diluted to a concentration of 10 ng/µl in PBS, and aliquots containing approximately 1 µg of antigen or PBS alone were dispensed into alternate rows of 96-well ELISA plates. The conditions of the assay were exactly as previously described (Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference), except primary antisera were pre-absorbed with non-recombinant (AcNPV) baculovirus-infected Sf-9 cell lysate diluted in blocking solution (2% v/v) prior to testing. All antisera were tested in duplicate, on numerous occasions, at dilutions ranging from 1:1000 to 1:128,000. Absorbance values for all of the rabbit anti-VLP antisera shown in FIG. 17 were obtained at the optimal dilution for these antisera of 1:16,000. Absorbance values for the anti-PVL1 common antigen and HPV-11 whole virion rabbit antisera were obtained at lower dilution (1:1,000). Specific absorbance values were determined by subtracting control values (PVS wells) from experimental values (antigen-containing wells) for each replicate, and mean (405 nm) absorbance values were determined.

EXAMPLE XIII

VLP ELISA

VLPs were tested in ELISA immunoassay to assess their ability to detect specific antibodies in patients' sera, and the results were compared with results previously obtained using the same sera in an HPV-11 whole virion ELISA immunoassay (Bonnez et al., *J. Med. Virol.* 39:340–344 (1993), which is hereby incorporated by reference). The antigen was diluted in phosphate-buffered saline (PBS) to give an amount equivalent to that of the amount used in the previous whole virion ELISA (Bonnez et al., *J. Med. Virol.* 39:340–344 (1993), which is hereby incorporated by reference), and either the antigen solution or PBS without any antigen was aliquoted into alternate rows of 96-well plates. After coating for 16 hours at 4° C., these solutions were aspirated and wells were blocked with diluent/blocking solution (Kirkegaard and Perry Laboratories, Inc., Gaithersburg, Md.) at room temperature for 2 hours. A total of 59 human sera (43 patients, 16 controls) previously tested by HPV-11 whole virus particle ELISA (Bonnez et al., *J. Med. Virol.* 39:340–344 (1993), which is hereby incorporated by reference) were diluted 1:100 in diluent/blocking solution and 100 $\mu$l aliquots were added to wells treated either with PBS alone or with antigen solution (two replicates per serum sample). Plates were incubated at room temperature for 90 minutes, and then washed four times (wash solution, Kirkegaard and Perry Laboratories, Inc., Gaithersburg, Md.). Anti-human IgG-alkaline phosphatase conjugate (100 $\mu$l aliquots, diluted 1:5000, TAGO, Burlingame, Calif.), was added to each well and plates were incubated at room temperature for 90 minutes. Plates were washed four times and developed with alkaline phosphatase substrate (p-nitrophenyl phosphate in diethanolamine buffer). Specific absorbance at 405 nm for each serum sample was calculated by subtracting the value obtained from the PBS-treated well from the value obtained from the antigen-containing well for each replicate and mean replicate differences were calculated. In the whole virion ELISA discussed elsewhere herein, 42 patients' sera was analyzed (and 20 control sera) for changes in capsid antibody levels during the course of treatment (Bonnez et al., *J. Med. Virol.* 39:340–344 (1993), which is hereby incorporated by reference). All sera tested in the present ELISA study were collected at entry into the previous study. One of the patients' sera analyzed in the previous study were subsequently excluded for reasons related to treatment outcome and not to the results of the immunoassay. However, because the absorbance value of this serum was available, the serum was included in the present assay, which increased the number of patients' sera analyzed in the present ELISA study to 43. The number of control sera analyzed was reduced from 20 to 16 for logistical considerations pertaining to the assay.

The median [range] seroreactivity of the 16 control sera, expressed as an OD value, was 0.005 [−0.029, 0.025], compared to 0.024 [−0.063, 0.512] for the 43 patients' sera, a statistically significant difference (P=0.01; Mann-Whitney U test). Using the highest OD value in the control group as a cut-off, the sensitivity of the assay was 49% (P=$2\times10^{-4}$; Fisher's exact test). Therefore, the HPV-11 VLP ELISA was able to discriminate between patients with condyloma acuminatum and controls. In addition, there was excellent correlation (Pearson's product-moment r=0.87; P <$10^{-6}$) between sample seroreactivities with the HPV-11 VLP ELISA and the HPV-11 virion ELISA when all sera were included, or when only the 21 sera positive by HPV-11 VLP ELISA were considered (r=0.87; P<$10^{-6}$).

EXAMPLE XIV

Orally administered VLPs induce systemic immunoglobulin G (IgG) and IgA antibody responses.

Figure 18A:
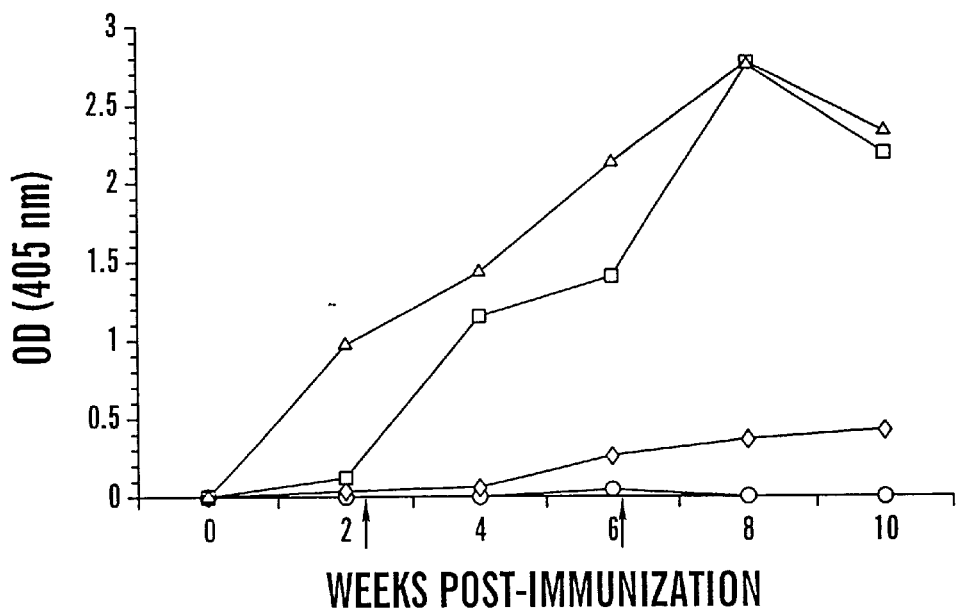
In FIG. 18A, bound antibodies were detected using anti-mouse IgG second antibody enzyme conjugate.

HPV-11 VLPs were produced by co-infecting insect cells with recombinant baculoviruses Ac11L1 and Ac11L2, which were constructed as previously described (Rose, R. C., et al., "Expression Of Human Papillomavirus Type 11 L1 Protein In Insect Cells: In Vivo And In Vitro Assembly of Virus-like Particles," *J. Virology* 67(4):1936–1944 (1993); Rose, R. C., et al., "Expression Of the Full-Length Products Of the Human Papillomavirus Type 6b (HPV-6b) and HPV-11 L2 Open Reading Frames By Recombinant Baculovirus, And Antigenic Comparisons With HPV-11 Whole Virus Particles," *J. Gen. Virol.* 71:2725–2729 (1990), which are hereby incorporated reference.) Purified VLPs were formulated in three dosage levels (100 $\mu$g, 50 $\mu$g, or 10 $\mu$g, in phosphate-buffered saline) and were administered intragastrically on three occasions over a six-week period to three groups of five female BALB/c mice (ages 8–10 weeks). Booster inoculations were also administered orally 14 and 41 days after primary immunizations. A fourth group of mice received no inoculations. Sera were collected every two weeks by retro-orbital puncture. Pre- and post-immune sera were pooled within each group of mice after collection, and were tested in an enzyme-linked immunosorbent assay (ELISA), as previously described (Li, M., et al., "Expression of The Human Papillomavirus Type 11 L1 Capsid Protein In *Escherichia Coli*: Characterization of Protein Domains Involved in DNA-Binding And Capsid Assembly," *J. Virology*, 71:2988–2995 (1997); White, W. I., et al., "In Vitro Infection And Type-Restricted Antibody-Mediated Neutralization Of Authentic Human Papillomavirus Type 16," *J. Virology*, 72:959–964 (1998), which are hereby incorporated by reference.) Specific absorbance Values (405 nm) were determined as previously described (Li, M., et al., "Expression of The Human Papillomavirus Type 11 L1 Capsid Protein In *Escherichia Coli*: Characterization of Protein Domains Involved in DNA-Binding And Capsid Assembly," *J. Virology*, 71:2988–2995 (1997); White, W. I., et al., "In Vitro Infection And Type-Restricted Antibody-Mediated Neutralization Of Authentic Human Papillomavirus Type 16," *J. Virology*, 72:959–964 (1998), which are hereby incorporated by reference.) Responses in the intermediate and high antigen dose groups became comparable within two weeks after the second booster inoculation (FIG. 18A).

Figure 18B:
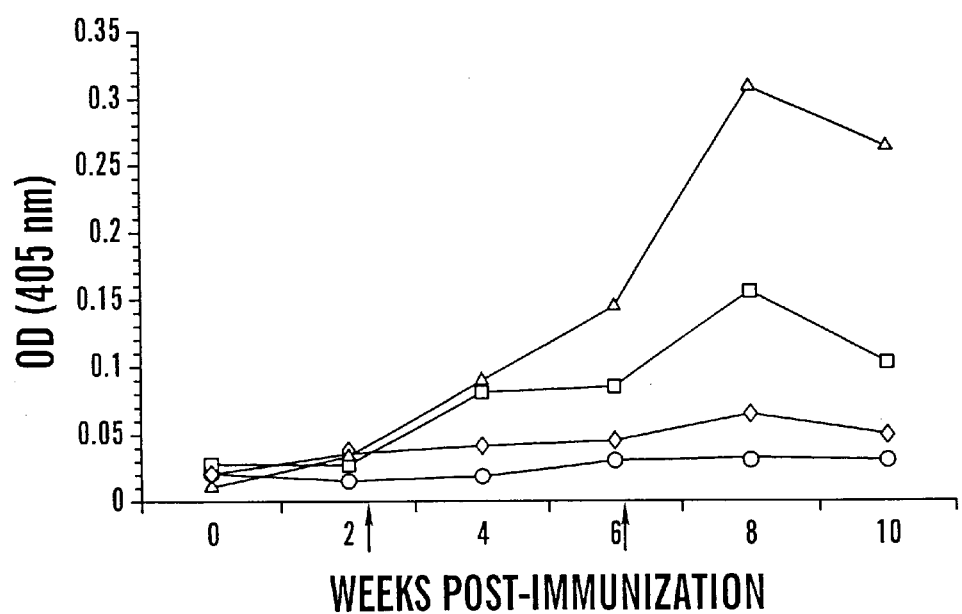
In FIG. 18B, sera were preabsorbed with goat anti-mouse IgG to remove antigen-specific IgG antibodies (Gray, J. J., et al., "Detection of Immunoglobulin M (IgM), IgA, and IgG Norwalk Virus-Specific Antibodies by Indirect Enzyme-Linked Immunosorbent Assay with Baculovirus-Expressed Norwalk Virus Capsid Antigen in Adult Volunteers Challenged With Norwalk Virus," *Journal of Clinical Microbiology* 32(12):3059–3063 (1994), which is hereby incorporated by reference), after which bound IgA antibodies were detected using anti-mouse IgA second antibody enzyme conjugate.

Serum IgA antibody responses were also detected in post-immune sera from immunized animals (FIG. 18B) after removing serum IgG antibodies by pre-treatment with goat anti-mouse IgG (Kirkegaard and Perry Laboratories, Inc., Gaithersburg, Md.) as described (Gray, J. J., et al., "Detection Of Immunoglobulin M (IgM), IgA, and IgG Norwalk Virus-Specific Antibodies By Indirect Enzyme-Linked Immunosorbent Assay With Baculovirus-Expressed Norwalk Virus Capsid Antigen In Adult Volunteers Challenged With Norwalk Virus," *Journal of Clinical Microbiology* 32(12):3059–3063 (1994), which is hereby incorporated by reference.) Although the kinetics of IgG and IgA antibody responses were comparable (FIGS. 18A,B), the relative magnitude of the IgG response was much greater than that of the IgA response (FIG. 18).

IgG subclass analysis (Southern Biotechnology Associates, Inc., Birmingham, Ala.) indicated there was no clear predominance of any specific subclass, although the appearance of IgG2a and IgG2b preceded that of IgGβ (Table 1).

TABLE 1

VLP Serum IgG Subclass Analysis

| Subclass | Weeks Post-Immunization ($A_{405}$) | | | | | |
|---|---|---|---|---|---|---|
| | 0 | 2 | 4 | 6 | 8 | 10 |
| IgG1 | 0.010 | 0.139 | 0.864 | 0.851 | 2.354 | 1.022 |
| IgG2a | 0.021 | 0.757 | 1.293 | 1.319 | 2.550 | 1.083 |
| IgG2b | 0.021 | 0.506 | 1.511 | 1.274 | 1.917 | 0.565 |
| IgG3 | 0.012 | 0.213 | 0.292 | 0.164 | 0.286 | 0.067 |

IgG2a has been shown to be a prominent component of murine immune responses to viral infections (Coutelier, J. P., et al., "Virally Induced Modulation of Murine IgG Antibody Subclasses," *J. Exp. Med.* 168(6):2373–2378 (1988), which is hereby incorporated by reference).

EXAMPLE XV

Antigenic specificities of orally induced serum VLP antibodies.

Figure 19:
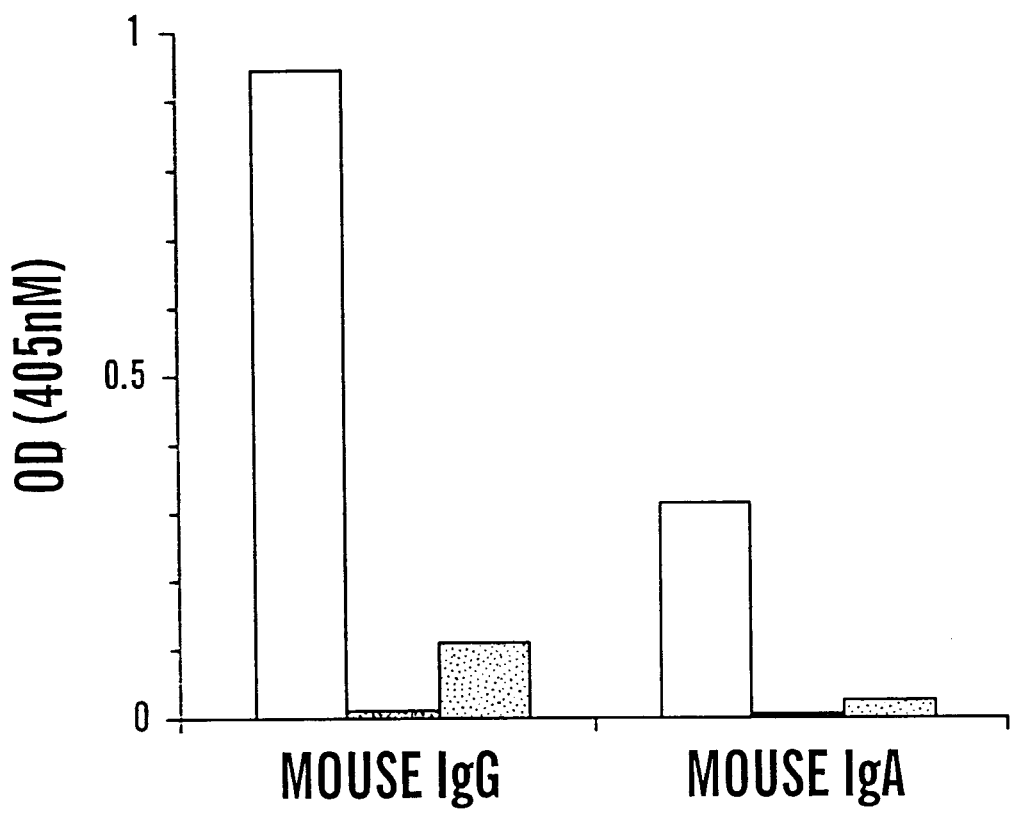
FIG. 19 shows the antigenic specificities of orally induced systemic VLP antibodies. Murine serum VLP antibodies were evaluated in an ELISA against HPV-11 native VLPs (white bars), HPV-11 denatured VLPs (black bars), and HPV-16 native VLPs (gray bars).

Orally induced antibodies were evaluated in an ELISA against native and denatured HPV-11 VLPs (Rose, R. C., et al., "Expression of Human Papillomavirus Type 11 L1 Protein in Insect Cells: in vivo and in vitro Assembly of Virus-like Particles," *J. Virology* 67(4):1936–1944 (1993), which is hereby incorporated by reference), and against heterologous native VLPs, as previously described (Rose, R. C., et al., "Serological Differentiation of Human Papillomavirus Types 11, 16 and 18 Using Recombinant Virus-Like Particles," *J. Gen. Virol.* 75:2445–2449 (1994), which is hereby incorporated by reference). Antigen denaturation was accomplished by diluting VLPs in carbonate buffer (pH 9.5; 0.01 mg/ml final concentration) followed by incubation in a boiling water bath (10 minutes) (Dillner, L, et al., "Antigenic and Immunogenic Epitopes Shared By Human Papillomavirus Type 16 and Bovine, Canine, and Avian Papillomaviruses," *J. Virology* 65(12):6862–6871 (1991), which is hereby incorporated by reference). Native VLP antigens were diluted in phosphate-buffered saline (PBS, pH 7.1) to the same final concentration and kept on ice prior to evaluation. As shown in FIG. 19, the specificities of orally induced serum IgG and IgA VLP antibodies were entirely dependent on native antigen conformation. Consistent with previously reported results (Rose, R. C., et al., "Serological Differentiation of Human Papillomavirus Types 11, 16 and 18 Using Recombinant Virus-Like Particles," *J. Gen. Virol.* 75:2445–2449 (1994), which is hereby incorporated by reference), orally induced HPV-11 VLP antibodies were highly immunoreactive with VLPs of the same type used for immunization, but were not immunoreactive by ELISA with VLPs of a heterologous HPV genotype (FIG. 19).

EXAMPLE XVI

Epitope-Blocking ELISA.

Figure 20A:
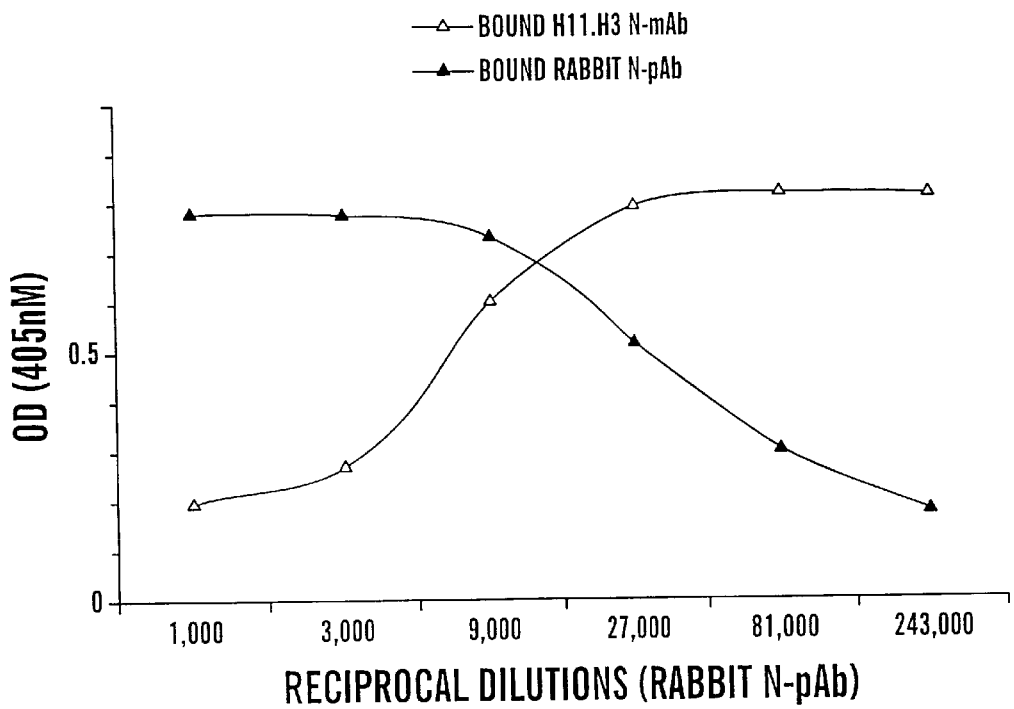
In FIG. 20A, HPV-11 VLPs (250 ng/well) were reacted with serial three-fold dilutions of Rabbit N-pAb (Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference) as indicated, and then were reacted with H11.H3 N-mAb held at constant dilution (1:180,000).
Figure 20B:
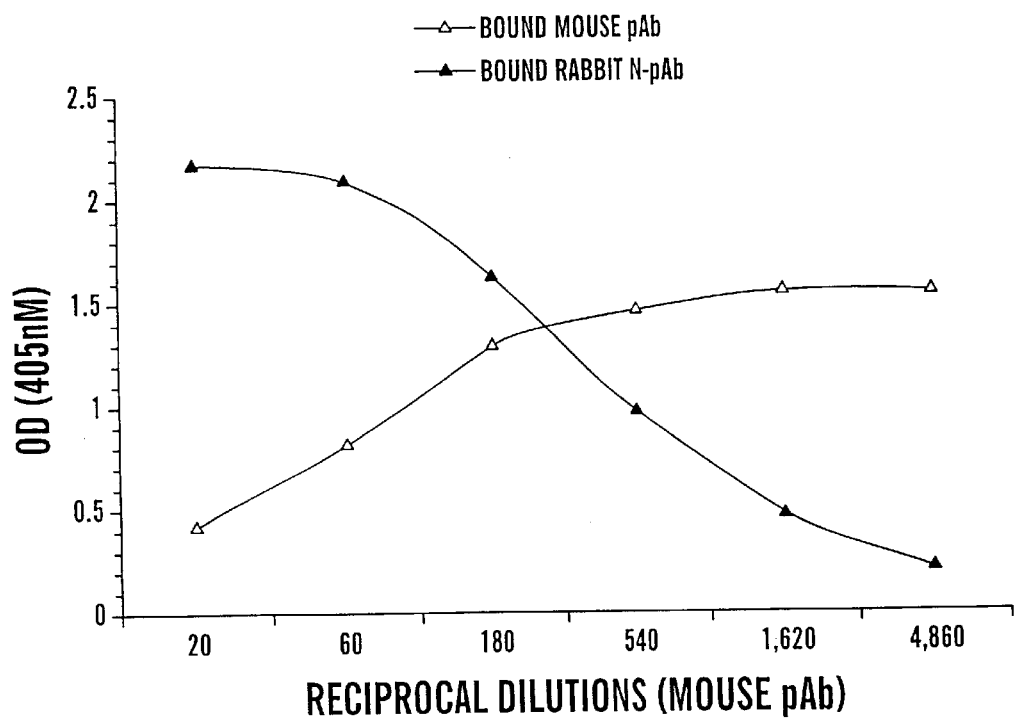
In FIG. 20B, HPV-11 VLPs (250 ng/well) were reacted with serial three-fold dilutions of murine post-immune VLP antibodies as indicated, and then were reacted with rabbit N-pAb held at constant dilution (1:9,000).

A VLP epitope-blocking ELISA was developed as a surrogate assay for detecting antibody-mediated virus-neutralizing activity. In this assay, an unknown antibody preparation is evaluated for the ability to prevent homologous VLP binding by antibodies that are known to neutralize homologous infectious virions; blockade of the neutralizing domain is interpreted as evidence of neutralizing activity in the unknown. The epitope-blocking assay requires that the unknown and virus-neutralizing antibodies be raised in alternate host species. The ability of rabbit HPV-11 virion-neutralizing polyclonal antibodies (N-pAb) (Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference) to block the epitope recognized by a previously characterized HPV-11 virion neutralizing monoclonal antibody (N-mAb), H11.H3 (Christensen, N. D., et al., "Monoclonal Antibody-Mediated Neutralization of Infectious Human Papillomavirus Type 11," *J. Virology* 64(11):5678–5681 (1990), which is hereby incorporated by reference) was tested. Serial three-fold dilutions of Rabbit HPV-11 N-pAb were tested in duplicate wells containing 250 ng of HPV-11 VLPs. Following this, pre-titered H11.H3 was diluted below the level of antigen saturation (i.e., 1:180,000) and added to wells containing rabbit N-pAb/VLP complexes. Lastly, relative amounts of bound N-pAb versus bound N-mAb were determined by adding anti-rabbit or anti-mouse IgG-alkaline phosphatase enzyme conjugates (Kirkegaard and Perry Laboratories, Gaithersburg, Md.) to parallel rows. As expected, low dilutions of rabbit N-pAb efficiently blocked H11.H3 VLP binding (FIG. 20A), suggesting that the rabbit HPV-11 N-pAb contained the neutralizing antigenic specificity defined by H11.H3. To further validate the assay, HPV-16 virion neutralizing monoclonal and polyclonal antibodies (Christensen, N. D., et al., "Surface Conformational and Linear Epitopes on HPV-16 and HPV-18 L1 Virus-Like Particles as Defined By Monoclonal Antibodies," *Virology* 223(1):174–184 (1996); White, W. I., et al., "In Vitro Infection and Type-Restricted Antibody-Mediated Neutralization of Authentic Human Papillomavirus Type 16," *J. Virology* 72:959–964 (1998), which are hereby incorporated by reference) were evaluated in a similar manner, and comparable results were obtained. Serial dilutions of the murine antibodies produced in the present study were evaluated against a sub-saturating dilution of pre-titered rabbit HPV-11 N-pAb (1:9,000). Results indicated that, at low dilutions, orally induced HPV-11 VLP antibodies efficiently blocked rabbit N-pAb VLP binding (FIG. 20B), which suggested that a potentially protective humoral response may be induced after oral VLP immunization.

RESULTS

Figure 8:
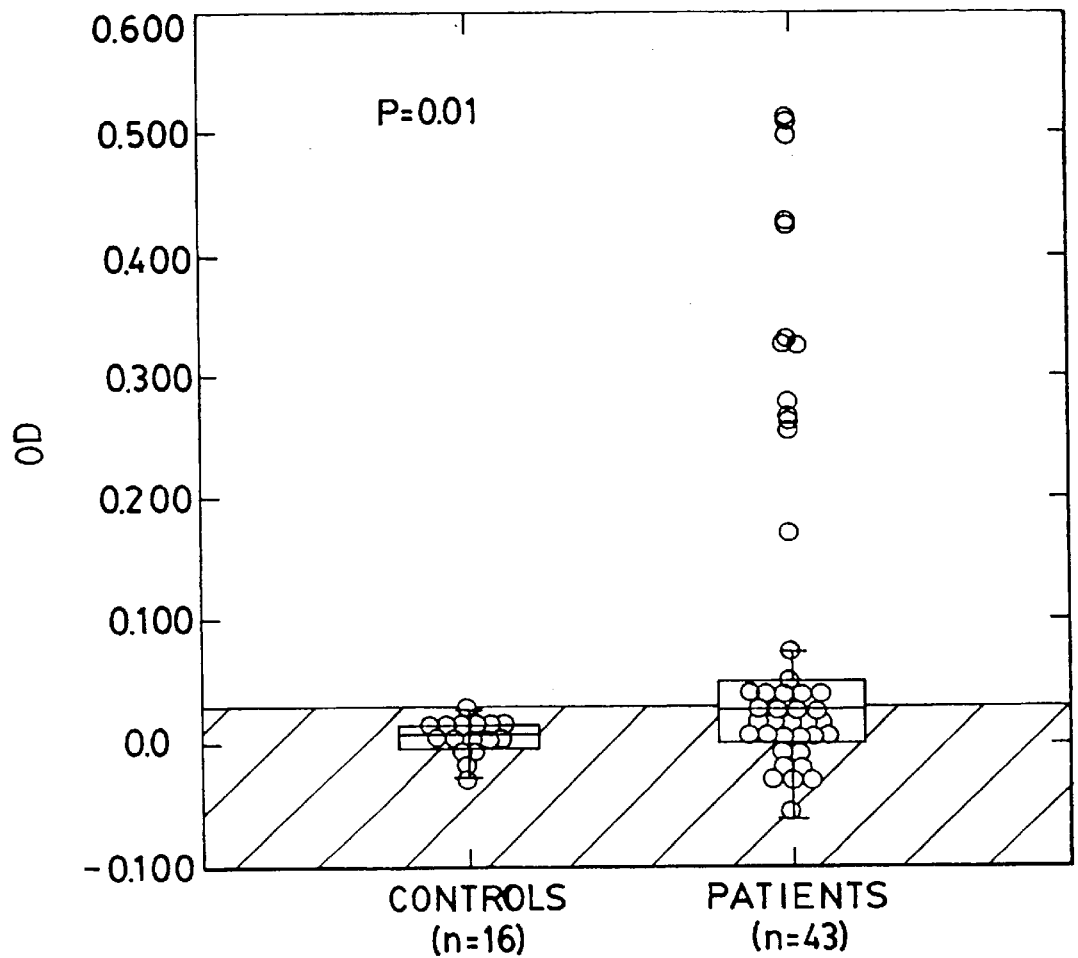
FIG. 8 shows seroreactivity of condyloma acuminatum patients to HPV-11 L1 VLPs.
Figure 9:
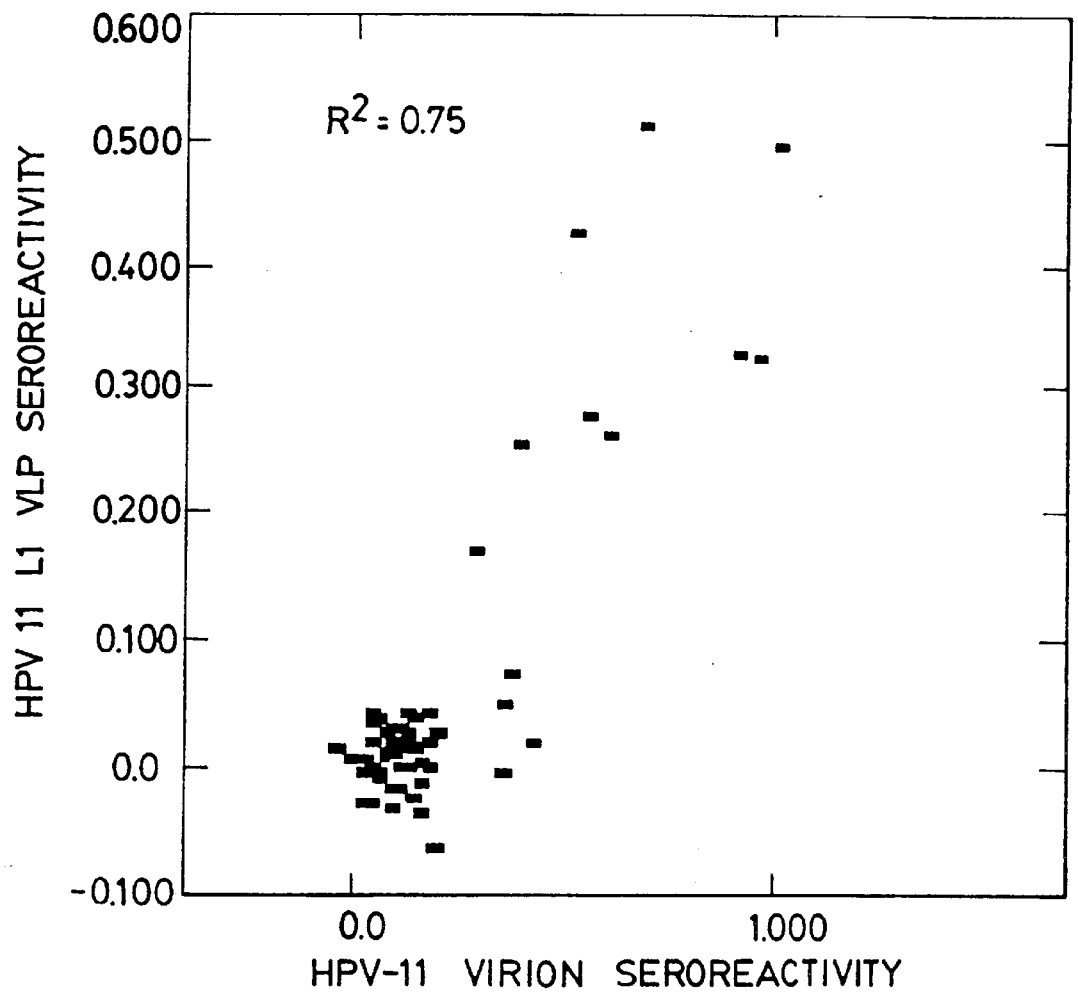
FIG. 9 shows correlation between the seroreactivities to HPV-11 virions and VLPs.

Immunologic observations suggest that recombinant L1 adopts a native conformation. The rabbit antiserum raised against the denatured L1 common antigen was immunoreactive only with denatured recombinant L1 (i.e., by Western blot), whereas the rabbit antiserum raised against non-denatured whole virus particles reacted only with non-denatured recombinant L1 (i.e., by immunodotblot). Furthermore, human sera from condyloma acuminatum patients which were reactive with HPV-11 virions in an ELISA according to Bonnez et al., "Use of human papillomavirus type 11 virions in an ELISA to detect specific antibodies in humans with condylomata acuminata," *J. Gen. Virol.* 72:1343–1347 (1991), which is hereby incorporated by reference, also reacted with non-denatured HPV-11 recombinant L1 (FIGS. 4, 8 & 9). Therefore, it appears that the conformational epitopes of the VLPs of the invention are similar to those present in native HPV-11 virions, which are recognized by the human immune system during natural infection. Several studies of papillomavirus serology demonstrate that conformational epitope antibody specificities are good indicators of papillomavirus infection (Bonnez et al., "Use of human papillomavirus type 11 virions in an ELISA to detect specific antibodies in humans with condylomata acuminata," *J. Gen. Virol.* 72:1343–1347 (1991); Bonnez et al., "Evolution of the antibody response to human papillomavirus type 11 (HPV-11) in patients with condyloma acuminatum according to treatment response," *J. Med. Virol.* 39:340–44 (1993); Bonnez et al., "Antibody-mediated neutralization of human papillomavirus type 11 (HPV-11) infection in the nude mouse: Detection of HPV-11 mRNAs by the polymerase chain reaction," 1992, *J. Inf. Dis.* 165:376–380 (1992); Christensen et al., "Detection of human serum antibodies that neutralize infectious human papillomavirus type 11 virions," *J. Gen. Virol.* 73:1261–1267 (1992); Kienzler et al., "Humoral and cell-mediated immunity to human papillomavirus type 1 (HPV-1) in human warts," *Br. J. Dermatol.* 108:665–672 (1983); and Steele et al., "Humoral assays of human sera to disrupted and nondisrupted epitopes of human papillomavirus type 1," *Virology* 174:388–398 (1990), which are hereby incorporated by reference). These specificities can also play a significant role in viral pathogenesis. For instance, a rabbit antiserum directed against whole HPV-11 particles neutralizes HPV-11 infectivity (Bonnez et al., "Antibody-mediated neutralization of human papillomavirus type 11 (HPV-11) infection in the nude mouse: Detection of HPV-11 mRNAs by the polymerase chain reaction," *J. Inf. Dis.* 165:376–380 (1992); and Christensen et al., "Antibody-mediated neutralization in vivo of infectious papillomavirus," *J. Virol.*, 64:3151–3156 (1990), which are hereby incorporated by reference). Furthermore, Christensen et al., "Detection of human serum antibodies that neutralize infectious human papillomavirus type 11 virions," *J. Gen. Virol.* 73:1261–1267 (1992), which is hereby incorporated by reference, using human sera reported a correlation between anti-whole HPV-11 virion antibody and serum neutralizing activity. Detection of such antibodies with the recombinant L1 VLPs of the present invention can have diagnostic and functional significance.

When taking into account construction of the recombinant baculovirus, some of the early recombinant baculoviruses applicants constructed had the correct L1 coding sequence, but were not producing detectable levels of L1 proteins. This caused applicants to look at the 3' untranslated regions of the HPV-11 and several other HPV L1 coding sequences. It was determined that a pentanucleotide mRNA degradation signal sequence, AUUUA, (Shaw G. and Kamen R., "A conserved AU sequence from the 3' untranslated region of GM-CSF mRNA mediates selective mRNA degradation," *Cell* 46:659–67 (1986); Cole M D. and Mango S E., "cis-acting determinants of c-myc mRNA stability," *Enzyme* 44:167–80 (1990); Shyu A B et al., "Two distinct destabilizing elements in the c-fos message trigger deadenylation as a first step in rapid mRNA decay," *Genes & Development* 5:221–31 (1991); Savant-Bhonsale S. and Cleveland D W., "Evidence for instability of mRNAs containing AUUUA motifs mediated through translation-dependent assembly of a >20S degradation complex," *Genes & Development* 6:1927–37 (1992), which are hereby incorporated by reference) was within 30 nucleotides of the stop codon of the HPV-11 L1 coding sequence, and in addition, the other HPV types looked at had the AUUUA sequence in the vicinity of the L1 stop codon as well. If this sequence were removed, or a mutation introduced, the expression level of the L1 protein could be increased. Therefore, PCR primers to amplify the L1 coding sequence from HPV-11 genomic DNA which not only incorporated restriction enzyme sites for cloning, but also mutated the AUUUA pentanucleotide sequence 30 nucleotides downstream from the L1 stop codon as well were designed. Scaleup of this clone produced extremely high levels of L1 protein. Reports using the BEVS system have given levels of recombinant protein production in the range of 300–500 mg/liter of cell culture. In the present invention, levels for recombinant L1 protein production were much greater, about 600–800 mg/liter, possibly due to the removal of the L1 degradation signal sequence in the 3' untranslated region.

These results show that, under similar experimental conditions, post-immune sera from rabbits immunized with HPV-11 VLPs can block HPV-11 infection of human tissue as effectively as sera obtained from rabbits immunized with HPV-11 whole virions. The blockage, which was not observed with the respective preimmune sera, was associated with the absence of early viral gene expression. Therefore, the effect was consistent with classic viral neutralization, i.e., the prevention of virus penetration or decapsidation (Dimmock, 1993, *Neutralization of Animal Viruses*, Berlin: Springer-Verlag, which is hereby incorporated by reference).

To provide confirmation of HPV-11 neutralization by analysis of viral gene expression, all grafts were analyzed for the presence of the HPV-11 E1^E4 spliced mRNA transcript (data not shown), as previously described in Bonnez et al., *J. Inf. Dis.* 165:376–380 (1992), which is hereby incorporated by reference. The E1^E4 mRNA was detected in 10/12 (83%) and 0/12 (0%) of the grafts from groups pre-treated with pre- or post-immune VLP sera, respectively ($p<10^{-4}$). Similarly, for the control groups pre-treated with pre- or post-immune anti-whole virion sera, E1^E4 mRNA was detected in 8/11 (73%) and 0/11 (0%) grafts, respectively ($p=10^{-3}$). These results indicate that treatment of the viral inoculum with the post-immune VLP serum is associated with marked inhibition of graft growth and viral gene expression, effects which are consistent with immune neutralization. Thus, recombinant VLPs can induce a neutralization response similar in magnitude to the response obtained by immunization with infectious virus.

The HPV 16 L1-L2 VLPs described by Zhou et al., *Virology* 185:251–257 (1991), which is hereby incorporated by reference, were variable in size and smaller (35–40 nm in diameter) than either HPV virions (50–55) or baculovirus produced HPV 11 VLPs (50–55 nm; Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which is hereby incorporated by reference). These morphologic characteristics are quite different from those of the VLPs described in the present invention. Furthermore, using the method of the invention, HPV L1 protein alone is sufficient for the formation of particles whose biophysical characteristics and antigenic properties closely reflect those of native HPV virions.

Using a similar approach, Kimbauer, et al. reported inhibition of BPV-1-mediated transformation of mouse C127 cells in vitro by anti-BPV-1 VLP antibodies (Kimbauer et al., *Proc. Natl. Acad. Sci. USA* 89:12180–12184 (1992), which is hereby incorporated by reference.) The results obtained in that system support the results reported in the present invention, in which applicants have demonstrated neutralization using a genital HPV and it's normal target tissue. Although concordance of results from the BPV-1/C127 cell assay and the athymic mouse bovine fetal skin xenograft system has been reported as previously described by Ghim et al., *Int. J. Cancer* 49:285–289 (1993), which is hereby incorporated by reference, the BPV-1/C127 mouse fibroblast system is non-productive, and therefore neutralization can only be inferred from the absence of transformed foci in vitro. In addition, BPV-1 does not naturally infect mice, and the mechanism by which it gains entry into C127 cells may differ from the mechanism involved in the natural infection process. In contrast, the athymic mouse model used in the present study relies on infection by a genital HPV of its natural target tissue as previously described by Kreider et al., *Nature* 317:639–641 (1985), which is hereby incorporated by reference; the infected graft is maintained in vivo and morphologic and histologic transformation of the infected graft is accompanied by the production of infectious virions. (See Kreider et al., *J. Virol.* 61:590–593 (1987), which is hereby incorporated by reference.) Antibody-mediated graft growth inhibition as previously described by Bonnez et al., *J. Inf. Dis.* 165:376–380 (1992); Christensen et al., *J. Virol.* 64:3151–3156 (1990); Christensen et al., *Virus Research* 21:169–179; Christensen et al., *J. Virol.* 64:5678–5681 (1990); and Christensen et al., *J. Gen. Virol.* 73:1261–1267 (1992), which are hereby incorporated by reference, and immunocytochemical and molecular biologic evidence of inhibition of viral gene expression has been well documented, as previously described by Bonnez et al., *J. Gen. Virol.* 72:1343–1347 (1991); and Bonnez et al., *J. Inf. Dis.* 165:376–380 (1992), which are hereby incorporated by reference. Therefore, observations made in the athymic mouse system may more accurately reflect the events that occur in the natural infection.

Neutralizing antibodies to HPV-11 have been identified in humans with condyloma acuminatum as previously described by Christensen et al., *J. Gen. Virol.* 73:1261–1267 (1992), which is hereby incorporated by reference, but their biological significance is unknown. If neutralization proves to be a protective immunologic effector mechanism against papillomavirus infections in vivo, then immunization with recombinant VLPs may provide protective immunity to individuals at risk for infection. Applicant's results suggest that the magnitude of neutralization activity of HPV-11 VLP antibodies is similar to that of antibodies specific for HPV-11 infectious virions. Therefore, VLPs appear to be good vaccine candidates. However, the degree of cross-reactivity of capsid conformational determinants among different HPV types is not yet known and may be low as previously described by Gissmann et al., *Virology* 76:569–580 (1977); Gross et al., *Oncoienic Viruses*, Pergamon Press, New York (1983); Hagensee et al., *J. Virol.* 67:315–322 (1993); Howley et al., "Papillomavirinae and their replication," Chap. 58. p. 1625–1650, in B. N. Fields and D. M. Knipe (ed.), *Virology*, 2nd ed., Vol. 2. Raven Press, New York (1990); Kirnbauer et al., *Proc. Natl. Acad. Sci. USA*, 89:12180–12184 (1992); Kreider et al., *J. Virol.* 61:590–593 (1987); Kreider et al., *Nature* 317:639–641 (1985); and Orth et al., *J. Virol.*, 24:108–120 (1977), which are hereby incorporated by reference. Full characterization of the potential of recombinant VLPs for use as immunogens for the prevention of genital HPV disease will require further studies involving VLPs derived from other genital HPV types. It will be of particular important to determine if antibodies to heterologous genital HPV VLPs will be capable of neutralizing HPV infection.

With reference to FIG. 17, HPV-11 whole virus particle (B) and HPV-11 VLP antisera (C,D) reacted strongly with HPV-11 VLPs, but none of these antisera reacted with the HPV-16 or HPV-18 VLP preparations. Similarly, HPV-16 (E,F) and HPV-18 (G,H) L1 VLP rabbit antisera reacted only with homotypic VLPs. The specificities of these reactions were verified in preabsorption experiments, in which the immunoreactivity of each rabbit VLP antiserum was abrogated by preabsorption with homotypic, but not heterotypic, VLPs. None of the rabbit preimmune sera reacted with any of the VLP preparations. The antiPVL1 common antigen antiserum, which reacted well with recombinant L1 proteins by Western immunoblot (FIG. 15), reacted only slightly with native VLP preparations in the ELISA (FIG. 17A). This observation suggests that epitopes normally recognized by this antiserum are masked under the conditions of the ELISA assay, and that the L1 proteins tested in this assay are predominantly non-denatured.

The present invention has shown that L1 VLP epitopes of HPV-11, -16, and -18 are antigenically distinct. Although L2 capsid proteins were not present in these VLP preparations, it is likely that the observed antigenic difference between HPV types also applies to virions. L2 represents approximately 10% of the total protein content of HPV particles (Doorbar et al., *J. Virol.* 61:2793–2799 (1987), which is hereby incorporated by reference) and, although its exact location in the particle has not been determined (Baker et al., *Biophysical J.* 60:1445–1456 (1991), which is hereby incorporated by reference), recent studies have suggested that it may be required for DNA encapsidation (Zhou et al., *J. Gen. Virol.* 74:763–768 (1993), which is hereby incorporated by reference) and that a domain present in the relatively conserved amino terminal portion of the HPV-16 L2 amino acid sequence mediates non-specific DNA binding (Zhou et al., *J. Virol.* 68:619–625 (1994), which is hereby incorporated by reference). Although the remainder of the L2 amino acid sequence is very heterogeneous among papillomaviruses (Danos et al., *J. Invest. Dermatology* 83:7–11 (1990), which is hereby incorporated by reference), it is unclear if L2-specific antibodies react with intact virions (Komly et al., *J. Virol.* 60:813–816 (1986); and Hagensee et al., *J. Virol.* 67:315–322 (1993), which are hereby incorporated by reference). Thus, the L2 protein is not expected to alter substantially the results of the present study.

Previous studies have indicated that different HPV types can be distinguished from one another using serologic techniques. For example, antibodies reactive with plantar wart virions were found much more commonly in sera from patients with plantar warts than in sera from patients with either common, flat, anogenital, or laryngeal warts (Pfister & zur Hausen, *Int. J. Cancer* 21:161–165 (1978); Kienzler et al., 1983, *Brit. J. Dermatilogy* 108:665–672 (1983); and Viac et al., *J. Med. Virol.* 32:18–21 (1990), which are hereby incorporated by reference). Anisimova et al., 1990, also showed directly by immunoelectron microscopy that HPV-1 and HPV-2 are antigenically distinct. However, it also appears that other HPV types are antigenically related. For example, the detection of antibodies which specifically recognize HPV-11 virions in sera from patients with documented HPV-6 infection was previously reported (Bonnez et al., *J. Gen. Virol.* 72:1343–1347 (1991); and Bonnez et al., *Virol.* 188:384–387 (1992), which are hereby incorporated by reference). Due to the lack of available HPV virions from most HPV types, VLPs are at present the best tool available to explore antigenic relatedness among HPVs. Antigenic differences among HPV types are likely to reflect genetic diversity within the L1 coding sequence. Chan et al. constructed a papillomavirus phylogenetic tree that is based upon genetic divergence within a defined region of the papillomavirus L1 amino acid sequence (Chan et al, *J. Virol.*, 66:5714–5725 (1992), which is hereby incorporated by reference). Their work shows the relatively close evolutionary relationship between HPV-6 and HPV-11, which is consistent with potential cross-reactivity between HPV-6 and -11 capsids. On the other hand, HPV-16 and HPV-18, which have diverged extensively in their L1 sequences, are expected to have little antigenic cross-reactivity with each other or with HPV-11. Those predictions are consistent with the results of the present invention.

The biologic relevance of HPV capsid antigenic variability is unknown, but diversity of the capsid protein could account for papillomavirus tissue-specificity. The availability of recombinant VLPs from a variety of papillomaviruses may prove useful in the identification of putative host- and tissue-specific cellular receptors. In addition, VLPs should play an important role in the delineation of the antigenic characteristics of HPVs, and in the conduct of studies of immune responses to these viruses.

The present invention has been described in some detail by way of illustration and example for purposes of clarity of understanding, however, it will be obvious that certain changes and modifications may be practiced within the scope of the appended claims.

We claim:

1. A method of inducing an immune response in a mammal against papillomavirus comprising:

administering papillomavirus virus-like particles orally to a mammal in an amount sufficient to induce an immune response to the papillomavirus.

2. The method according to claim 1 firther comprising:

administering one or more vaccine booster inoculations of papillomavirus virus-like particles orally to the mammal.

3. The method according to claim 1, wherein the papillomavirus is a human papillomavirus.

4. The method according to claim 3, wherein the human papillomavirus is Human Papillomavirus Type 6.

5. The method according to claim 3, wherein the human papillomavirus is Human Papillomavirus Type 11.

6. The method according to claim 3, wherein the papillomavirus virus-like particles are administered with a pharmaceutically acceptable carrier.

* * * * *